United States Patent
Ryu et al.

(10) Patent No.: US 10,080,355 B2
(45) Date of Patent: Sep. 25, 2018

(54) INDUCIBLE ANIMAL MODELS OF STRESS BEHAVIOR

(71) Applicant: MAX-PLANCK-GESELLSCHAFT ZUR FÖRDERUNG DER WISSENSCHAFTEN E.V., München (DE)

(72) Inventors: Soojin Ryu, Heidelberg (DE); Rodrigo De Marco, Heidelberg (DE)

(73) Assignee: Soojin Ryu, Mainz (DE)

( * ) Notice: Subject to any disclaimer, the term of this patent is extended or adjusted under 35 U.S.C. 154(b) by 0 days.

(21) Appl. No.: 14/650,077

(22) PCT Filed: Dec. 5, 2013

(86) PCT No.: PCT/EP2013/075698
§ 371 (c)(1),
(2) Date: Jun. 5, 2015

(87) PCT Pub. No.: WO2014/086938
PCT Pub. Date: Jun. 12, 2014

(65) Prior Publication Data
US 2015/0282462 A1    Oct. 8, 2015

(30) Foreign Application Priority Data

Dec. 6, 2012 (EP) .................... 12195863

(51) Int. Cl.
*A01K 67/027* (2006.01)
*A61K 49/00* (2006.01)
*C12N 15/85* (2006.01)
*C12N 9/88* (2006.01)

(52) U.S. Cl.
CPC ...... *A01K 67/0278* (2013.01); *A01K 67/0275* (2013.01); *A61K 49/0008* (2013.01); *C12N 9/88* (2013.01); *C12N 15/8509* (2013.01); *A01K 2207/15* (2013.01); *A01K 2217/072* (2013.01); *A01K 2217/203* (2013.01); *A01K 2227/40* (2013.01); *A01K 2267/0356* (2013.01); *C12N 2800/90* (2013.01)

(58) Field of Classification Search
None
See application file for complete search history.

(56) References Cited

FOREIGN PATENT DOCUMENTS

| CN | 101983058 A | 3/2011 |
|---|---|---|
| WO | 2004069994 A2 | 8/2004 |
| WO | 2004069995 A2 | 8/2004 |
| WO | 2004070042 A1 | 8/2004 |
| WO | 2009097688 A1 | 8/2009 |
| WO | 2011051390 A1 | 5/2011 |
| WO | 2011064262 A1 | 6/2011 |
| WO | 2011154393 A1 | 12/2011 |
| WO | 2012061690 A2 | 5/2012 |

OTHER PUBLICATIONS

Portugues, et al. (2013) "Optogenetics in a transparent animal: circuit function in the larval zebrafish", Current Opinion in Neurobiology, 23: 119-26.*
Grammatopoulos (2012) "Insights in mechanisms of corticotropin-releasing hormone receptor signal transduction", British Journal of Pharmacology, 166(1): 85-97.*
De Marco, et al. (2013) "Optogenetic elevation of endogenous glucocorticoid level in larval zebrafish" Frontiers in Neural Circuits, 7(82): 1-11.*
Benedict J. Kolber et al: "Hypothalamic-pituitary-adrenal axis dysregulation and behavioral analysis of mouse mutants with altered glucocorticoid or mineralocorticoid receptor function", Stress, vol. 11, No. 5, Jan. 1, 2008 (Jan. 1, 2008), pp. 321-338.
Office Action dated Jul. 26, 2016 in a corresponding European application No. 13802343.7-1410.
Ghisleni, et al., "The role of CRH in behavioral responses to acute restraint stress in zebrafish", Progress in Nuero-Psychopharmacology and Biological Psychiatry, 36, 2012, pp. 176-182.
Moretz, et al., "Behavioral syndromes and the evolution of correlated behavior in zebrafish", Advance Access Publication, Mar. 5, 2007, pp. 556-563.
Aponte, et al., "AGRP neurons are sufficient to orchestrate feeding behavior rapidly and without training", Nature Neuroscience, vol. 14, No. 3, Mar. 2011, pp. 351-358.
Oswald, et al., "Strain-specific alteration of zebrafish feeding behavior in response to aversive stimuli", NIH Public Access, 2011, 18 pages.

(Continued)

*Primary Examiner* — Robert M Kelly
(74) *Attorney, Agent, or Firm* — Roberts Mlotkowski Safran Cole & Calderon, P.C.

(57) ABSTRACT

The present invention relates to a method of producing an inducible animal model of stress comprising genetically modifying a non-human vertebrate to express one or more protein(s) that can be activated by light in (a) cell(s) of the hypothalamic-pituitary-adrenal axis, wherein the protein(s) that can be activated by light are capable of inducing the release of (i) corticotrophin-releasing hormone (CRH) and/or arginine-vasopressin (A VP) from neurons in the paraventricular nucleus of the rostral hypothalamus; (ii) adrenocorticotropic hormone (ACTH) from corticotroph cells in the anterior pituitary; and/or (iii) glucocorticoids from cells in the adrenal cortex. The present invention further relates to an animal model of stress obtained by the method of the invention and the use of said animal model for screening for a compound for preventing, ameliorating or treating stress and/or stress-associated diseases. Further, the present invention also relates to a method of screening for a compound for preventing, ameliorating and/or treating stress and/or stress-associated diseases and methods of analyzing stress behavior in fish.

11 Claims, 13 Drawing Sheets

(56) References Cited

OTHER PUBLICATIONS

Figure 1:
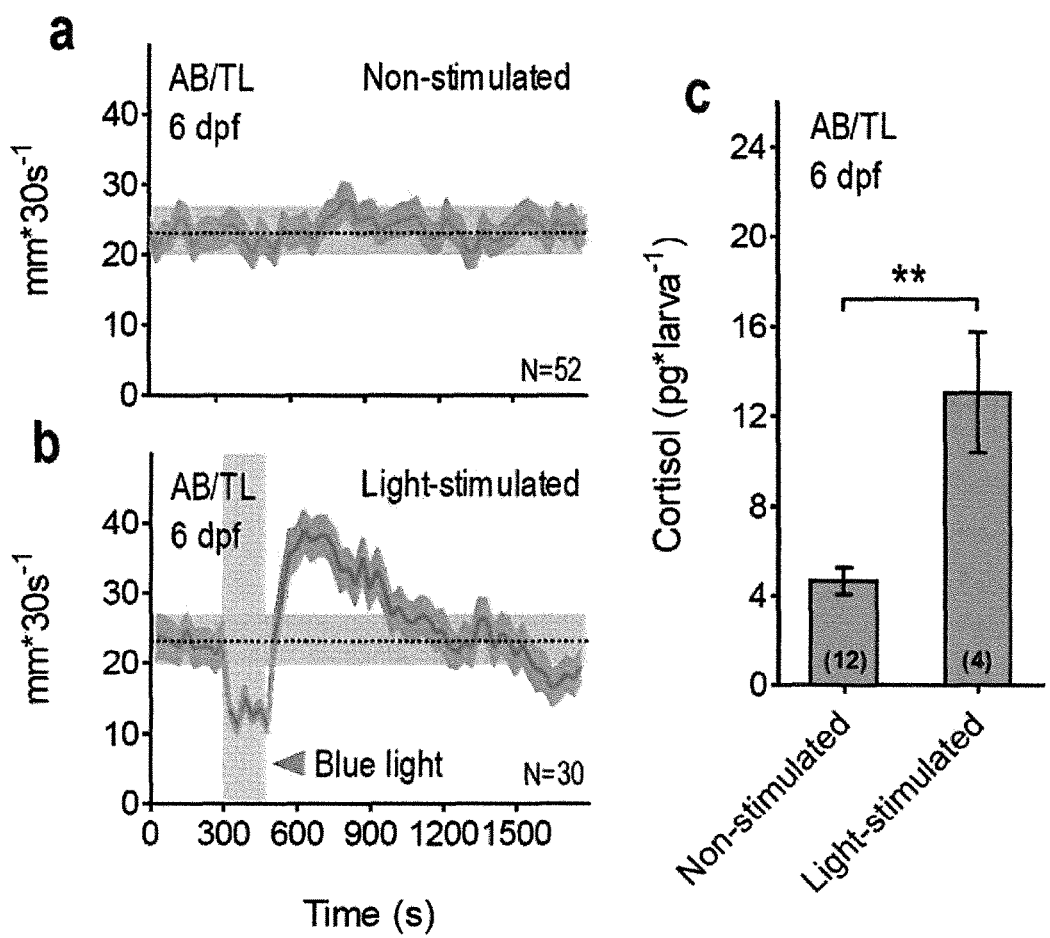
Figure 1:
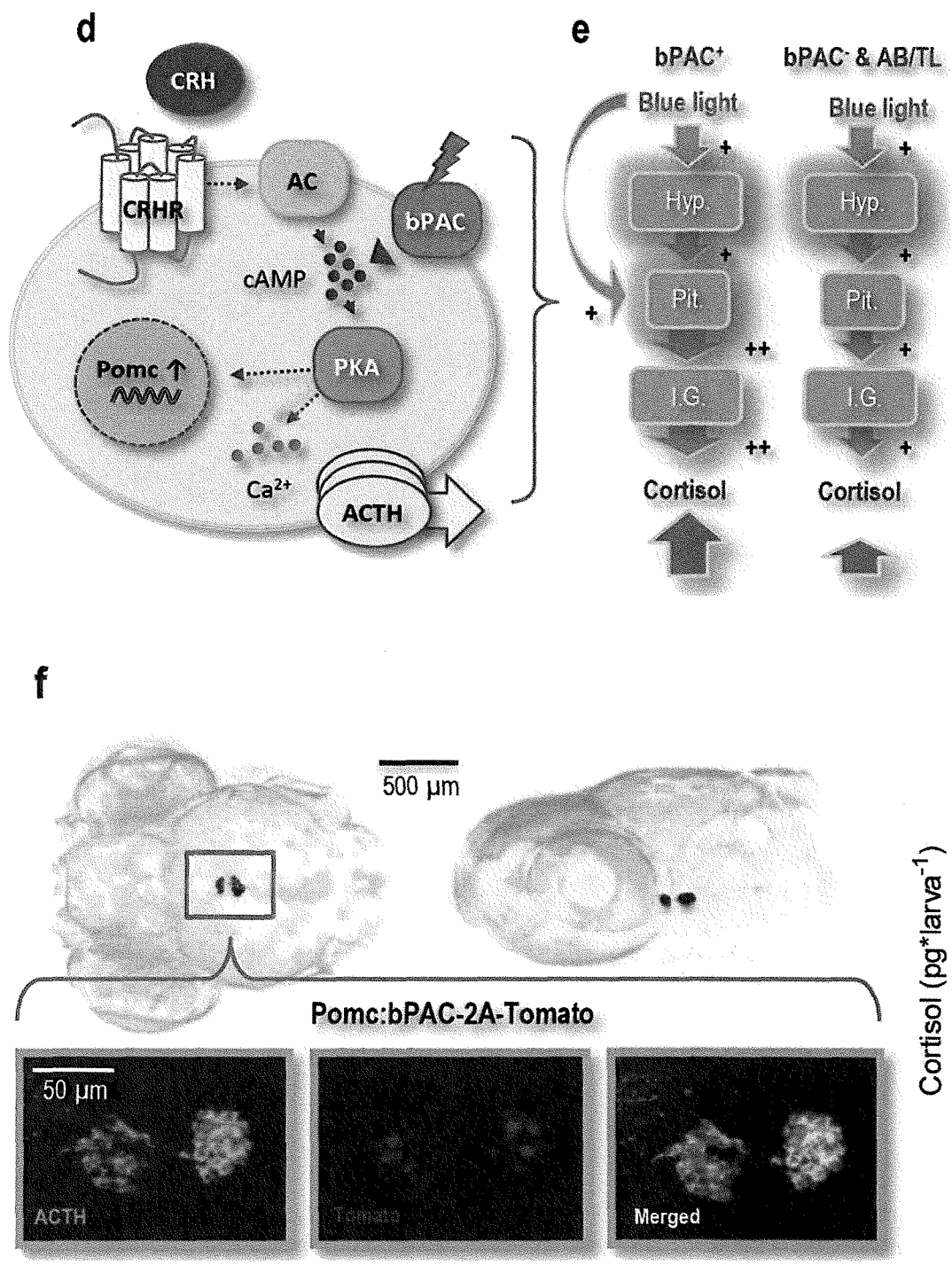
Figure 1:
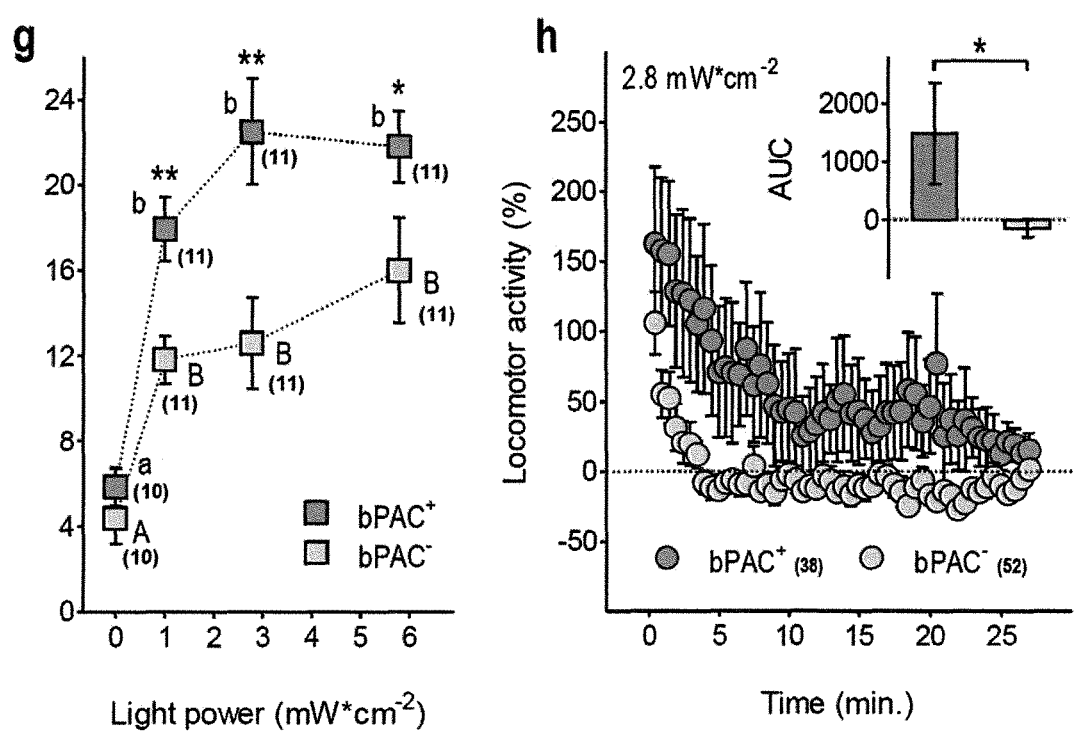

Yizhar, et al., "Optogenetics in Neural Systems", Neuron 71, Jul. 14, 2011, pp. 9-34.
Charmandari, et al., "Endocrinology of the Stress Response", Annu. Rev. Physiol., 2005, 67, pp. 259-284.
Alderman, et al., "Ontogeny of the corticotropin-releasing factor system in zebrafish", General and Comparative Endocrinology, 164, 2009, pp. 61-69.
Alsop, et al., "Development of the corticosteroid stress axis and receptor expression in zebrafish", Am J Physiol Regul Integr Comp Physiol, 294, 2008, pp. 711-719.
Alsop, et al., "The zebrafish stress axis: Molecular fallout from the teleost-specific genome duplication event", General and Comparative Endocrinology, 161, 2009, pp. 62-66.
Artz, et al., "CRF signaling: molecular specificity for drug targeting in the CNS", Trends in Pharmacological Sciences, vol. 27, No. 10, 2006, pp. 531-538.
Bale, et al., "Increased Depression-Like Behaviors in Corticotropin-Releasing Factor Receptor-2-Deficient Mice: Sexually Dichotomous Responses", The Journal of Neuroscience, Jun. 15, 2013, pp. 5295-5301.
Dallman, et al., "Corticosteroids and the Control of Function in the Hypothalamo-Pituitary-Adrenal (HPA) Axis", Annals of New York Academy of Sciences, 1994, pp. 22-30.
Chrousos, et al., "The Concepts of Stress and Stress System Disorders" JAMA, Mar. 4, 1992, pp. 1244-1252.
Mueller, et al., "Limbic corticotropin-releasing hormone receptor 1 mediates anxiety-related behavioral and hormonal adaptation to stress", Nature Neuroscience, vol. 6, No. 10, Oct. 2003, pp. 1100-1107.
De Kloet, et al., "Stress and the Brain: From Adaptation to Disease", Nature Reviews, Neuroscience, vol. 6, Jun. 2005, pp. 463-475.
Dirks, et al., "Overexpression of corticotropin-releasing hormone in transgenic mice and chronic stress-like autonomic and physiological alterations", European Journal of Neuroscience, vol. 16, pp. 1751-1760, 2002.
Groenink, et al., "HPA Axis Dysregulation in Mice Overexpressing Corticotropin Releasing Hormone", Society of Biological Psychiatry, 2002, pp. 875-881.
Lu, et al., "Conditional mouse mutants highlight mechanisms of corticotropin-releasing hormone effects on stress-coping behavior", Molecular Psychiatry, 2006, pp. 1028-1042.
Mueller, et al., "Mice with Mutations in the HPA-System as Models for Symptoms of Depression", Biol. Psychiatry, 2006, pp. 1104-1115.
Nagel, et al., "Channelrhodopsin-1: A Light-Gated Proton Channel in Green Algae", Science, vol. 296, Jun. 28, 2002, pp. 2395-2399.
Munck, et al., "Physiological Functions of Glucocorticoids in Stress and Their Relation to Pharmacological Actions", Endocrine Reviews, vol. 5, No. 1, 1984, pp. 25-44.
Raber, "Detrimental Effects of Chronic of Hypothalamic-Pituitary-Adrenal Axis Activation", Molecular Neurobiology, 1998, 23 pages.
Refojo, et al., "Glutamatergic and Dopaminergic Neurons Mediate Anxiogenic and Anxiolytic Effects of CRHR1", Science, 2011, 42 pages.
Smith, et al., "Corticotropin Releasing Factor Receptor 1-Deficient Mice Display Decreased Anxiety, Impaired Stress Response, and Aberrant Neuroendicrine Development", Neuron, vol. 20, pp. 1093-1102, 1998.
Ryu, et al., "Natural and Engineered Photoactivated Nucleotidyl Cyclases for Optogenetic Applications", The Journal of Biological Chemistry, Dec. 31, 2010, pp. 41501-41509.
Sapolsky, et al., : "How Do Glucocorticoids Influence Stress Responses? Integrating Permissive, Suppressive, Stimulatory, and Preparative Actions", Endocrine Reviews, pp. 55-89, 2000.
To, et al., "Pituitary-Interrenal Interaction in Zebrafish Interrenal Organ Development", Molecular Endocrinology, 21, 2007, pp. 472-486.
To, et al., Supplemental Data, Molecular Endocrinology, 21, 2007, pp. 472-486.
Stierl, et al., "Light Modulation of Cellular cAMP by a Small Bacterial Photoactivated Adenylyl Cyclase, bPAC, of the Soil Bacterium Beggiatoa", The Journal of Biological Chemistry, vol. 286, 2011, pp. 1181-1188.
Timpl, et al., "Impaired stress response and reduced anxiety in mice lacking a functional corticotropin-releasing hormone receptor 1", Nature Genetics, vol. 9, Jun. 19, 1998, pp. 162-166.
Weninger, et al. "Stress-induced behaviors require the corticotropin-releasing hormone (CRH) receptor, but not CRH", Proc. Natl. Acad. Sci., vol. 96, Jul. 1999, pp. 8283-8288.
Wendelaar Bonga, "The Stress Response in Fish", Physiological Reviews, vol. 77, Jul. 1997, pp. 591-625.
Steenbergen, et al., "The use of zebrafish model in stress research", Progress in Neuro-Psycopharmacology & Biological Psychiatry, vol. 35, No. 6, Oct. 13, 2010, pp. 1432-1451.
Del Bene, et al., "Optogenetics: A new enlightenment age for zebrafish neurobiology", Developmental Neurobiology, vol. 72, No. 3, Mar. 2012, pp. 404-414.
Amir-Zilbertstein, et al., "Homeodomain Protein Otp and Activity-Dependent Splicing Modulate Neuronal Adaptation to Stress", Neuron, vol. 73, No. 2, Jan. 2012, pp. 279-291.
Cheng, et al., "Using optogenetics to translate the "inflammatory dialogue" between heart and brain in the contet of stress", Neuroscience Bulletin, vol. 28, No. 4, Jun. 22, 2012, pp. 435-448.
Bakshi, et al., "Corticotropin-releasing hormone and animal models of anxiety: Gene-environment interactions", Biological Psychiatry, vol. 42, No. 12, pp. 1175-1198.
Wyart, et al., "Optogenetic dissection of a behavioural module in the vertebrate spinal cord", Nature, vol. 461, No. 14, Sep. 2009, pp. 407-411.
Arrenberg, et al., "Optical control of zebrafish behavior with halorhodopsin", PNAS, vol. 106, No. 42, Oct. 20, 2009, pp. 17968-17973.
Arrenberg, et al., "Optogenetic control of cardiac function", Science, vol. 330, Nov. 12, 2010, pp. 971-974.
Schoonheim, et al., "Optogenetic Localization and Genetic Perturbation of Saccade-Generating Neurons in Zebrafish", The Journal of Neuroscience, May 19, 2010, pp. 7111-7120.
Schroder-Lang, et al., "Fast manipulation of cellular cAMP level by light in vitro", Nature Methods, vol. 4, No. 1, Jan. 2007, pp. 39-42.
Anonymous, "Hypothalamic-pituitary-adrenal axis", Wikipedia, Dec. 3, 2012, XPo55372922.
Ruggiero C, Lalli E, "Impact of ACTH Signaling on Transcriptional Regulation of Steroidogenic Genes", Frontiers in Endocrinology, Mar. 29, 2016, vol. 7, p. 24.
Clark, Barbara J, "ACTH Action on StAR Biology," Frontiers in Neuroscience, Dec. 6, 2016, vol. 10, p. 547.
Sun Linli et al., "Construction of POMC: Research of EGFP as a new environmental endocrine disrupting effect evaluation platform", The 5th National Conference on Environmental Chemistry, Dec. 31, 2009, p. 630.

\* cited by examiner

INDUCIBLE ANIMAL MODELS OF STRESS BEHAVIOR

CROSS-REFERENCE TO RELATED APPLICATIONS

The present Application is a U.S. National Phase of PCT/EP2013/075698 filed on Dec. 5, 2013 which claims priority to European patent application No. 12195863.1 filed on Dec. 6, 2012. The disclosure of the PCT Application is hereby incorporated by reference into the present Application.

The present invention relates to a method of producing an inducible animal model of stress comprising genetically modifying a non-human vertebrate to express one or more protein(s) that can be activated by light in (a) cell(s) of the hypothalamic-pituitary-adrenal axis, wherein the protein(s) that can be activated by light are capable of inducing the release of (i) corticotrophin-releasing hormone (CRH) and/or arginine-vasopressin (AVP) from neurons in the paraventricular nucleus of the rostral hypothalamus; (ii) adrenocorticotropic hormone (ACTH) from corticotroph cells in the anterior pituitary; and/or (iii) glucocorticoids from cells in the adrenal cortex. The present invention further relates to an animal model of stress obtained by the method of the invention and the use of said animal model for screening for a compound for preventing, ameliorating or treating stress and/or stress-associated diseases. Further, the present invention also relates to a method of screening for a compound for preventing, ameliorating and/or treating stress and/or stress-associated diseases and methods of analyzing stress behavior in fish.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Stress is a state of threatened homeostasis that organisms counteract by activating a repertoire of physiological and behavioral responses, as a whole referred to as the stress response (Johnson et al., 1992). The stress response involves two systems. The sympatho-adrenomedullar system, responsible for immediate reactions, and the hypothalamic-pituitary-adrenal (HPA) axis, responsible for energy reallocation and stress response termination (de Kloet et al., 2005). In response to stress, neurons in the paraventricular nucleus (PVN) of the rostral hypothalamus release corticotrophin-releasing hormone (CRH) and arginine-vasopressin (AVP) into the hypothalamo-pituitary portal circulation. Receptor binding of these signals in the anterior pituitary triggers the release of adrenocorticotropic hormone (ACTH) from corticotroph cells into the blood. ACTH then stimulates the secretion of glucocorticoids by cells in the adrenal cortex. Glucocorticoids are the final effectors of the HPA-axis (de Kloet et al., 2005), with targets in the periphery and the central nervous system (Munck et al., 1984), including the cells in the hypothalamus that triggered the stress response in the first place, thus forming a negative feedback inhibiting CRH and ACTH release (Dallman et al., 1994). Physiological stress correlates involve changes in the immune system, cardiovascular function and metabolism (Munck et al., 1984, Sapolsky et al., 2000), whereas behavioral stress correlates involve increased cognition and focused attention, reduction in reproductive behavior, and suppression of appetite and feeding (Chrousos and Gold, 1992).

While crucial for the survival of an animal on a short term, inadequate or excessive activation of the stress response can be detrimental, and obesity, depression, and dementia have been associated with stress response dysfunction (Raber, 1998).

Despite its importance, both the development of a fully functional stress response system and the molecular mechanisms responsible for stress response dysfunction remain uncertain. Thus, an ability to control and detect stress response precisely in an animal model would be invaluable in testing and developing medications for stress-related disorders. At present, a good animal model system to test stress dysfunction in a high throughput manner is still lacking. Current mouse models of chronic stress are very labor-intensive to generate and the protocol and the resulting phenotypes vary greatly depending on in which laboratory the experiments have been carried out. In particular, animal models that specifically target the HPA axis utilize gene knockout or overexpression and do not provide temporal control. For example, due to the central role of CRH in the regulation of the stress response and its connection to affective disorders, a large amount of work has focused on generating mouse models with impaired CRH signaling (Muller and Holsboer 2006). However, global mouse knockouts of CRH do not reveal impairment in stress-induced behaviors, which may suggest the role of other CRH-like molecules in mediating the stress response or existence of compensatory mechanisms in these mutants (Weninger et al. 1999). Global CRH receptor 1 (CRHR1) or CRH receptor 2 (CRHR2) deficient mice, on the other hand, display anxiety and impaired stress response (Bale and Vale 2003; Smith et al. 1998; Timpl et al. 1998). Similarly, global CRH-overexpressing mice show HPA axis dysregulation and chronic stress-like autonomic and physiological alterations (Dirks et al. 2002; Groenink et al. 2002). However since CRH and CRH receptors are expressed in multiple sites in the brain, these studies could not separate the hypothalamic neuroendocrine function of CRH from its roles in regulating diverse behaviors through its extra hypothalamic receptor sites.

To overcome this problem, forebrain-specific CRH-overexpressing mice (Lu et al. 2008) as well as limbic system specific CRHR1 knockout mice have been generated (Muller et al. 2003). More recently targeted deletion of CRHR1 in specific neuronal population identified distinct roles of CRHR1 in glutamatergic and dopaminergic neurons (Refojo et al. 2011). While these studies have made important contributions to understanding CRH function, one important limitation lies in the fact that these genetic manipulations do not allow a temporal control. Even in specific cell types, knockout or overexpression of the gene function occurs constitutively over a long period of time. This may trigger a compensatory mechanism, which changes the neural circuit in a way that would not normally happen. To model acute, repeated or even a long term exposure to stress that occurs in a human population and has causal link to depression, what is required is an animal model where CRH activity can be temporally controlled only in a specific cell population.

Similarly no method exists so far for inducible inactivation of pituitary or adrenal cortical functions.

Thus, despite the fact that a lot of effort has been invested into elucidating the mechanisms underlying stress responses, no animal model exists so far that enables the easy, temporally controlled and non-invasive analysis of stress behavior in vivo. Accordingly, there is still a need to provide such animal models and test methods, for example for drug discovery.

This need is addressed by the provision of the embodiments characterized in the claims.

Accordingly, the present invention relates to a method of producing an inducible animal model of stress comprising genetically modifying a non-human vertebrate to express one or more protein(s) that can be activated by light in (a) cell(s) of the hypothalamic-pituitary-adrenal axis, wherein the protein(s) that can be activated by light are capable of inducing the release of (i) corticotrophin-releasing hormone (CRH) and/or arginine-vasopressin (AVP) from neurons in the paraventricular nucleus of the rostral hypothalamus; (ii) adrenocorticotropic hormone (ACTH) from corticotroph cells in the anterior pituitary; and/or (iii) glucocorticoids from cells in the adrenal cortex.

The term "inducible animal model of stress", as used herein, refers to an animal wherein stress can be activated by the researcher when required. In accordance with the present invention, the animal expresses one or more protein(s) that can be activated by light, as detailed herein below. Light-activation of said protein(s) initiates signaling along the hypothalamic-pituitary-adrenal (HPA) axis, thus imitating the naturally occurring stress response observed in animals.

It is well known in the art that in different vertebrates differences in the hypothalamic-pituitary-adrenal (HPA) axis responsible for energy reallocation and stress response termination exist. For example, in teleosts, it is the inter-renal gland that produces corticosteroids (with cortisol being the central end product) and, thus, their stress axis is often referred to as the hypothalmic-pituitary-interrenal (HPI) axis (Wendelaar Bonga, 1997). In accordance with the present invention it is intended that these variations fall under the term HPA, even if not explicitly discussed in each case. Thus, when referring to HPA, also HPI is included.

In accordance with the present invention, the animal is a genetically modified non-human vertebrate. The non-human vertebrate may be any non-human vertebrate. Preferably, the non-human vertebrate is a non-human mammal, an avian, a fish or a frog. Even more preferably, the non-human mammal is selected from the group consisting of rodents, dogs, felids, primates, rabbits, pigs and ruminants; the avian is selected from the group consisting of chickens, turkeys, pheasants, ducks, geese, quails and ratites including ostriches, emus and cassowaries; the fish is selected from the group consisting of zebrafish, medaka, trout, salmon, tuna or herring; and the frog is selected from the genus *Xenopus*.

The term "genetically modifying a non-human vertebrate", as used herein, refers to altering the genetic make-up of said non-human vertebrate. In accordance with the present invention, such alterations refer to the introduction of (a) nucleic acid sequence(s) encoding one or more protein(s) that can be activated by light, such that it/they can be, and are, transcribed and translated into the corresponding (functional) proteins.

A number of different strategies are known in the art for the modification of the genome of a non-human vertebrate, all of which may be employed in accordance with the present invention. For example, the nucleic acid sequence(s) encoding the one or more protein(s) that can be activated by light can be introduced as (a) transgene(s) into the genome, by homologous recombination (HR) techniques for targeted gene modifications or by the use of gene trapping or of transposon-mediated mutagenesis.

For the generation of traditional transgenic animals, the nucleic acid sequence encoding the one or more protein(s) that can be activated by light is injected into fertilized eggs of the respective animal. Embryos are implanted into the uterus of a surrogate mother and the respective nucleic acid sequence will be expressed by some of the offspring. This conventional transgenic approach offers the advantage of being relatively straightforward and inexpensive while high levels of gene expression can be achieved. With this method, the site of integration is random, thus not allowing for a targeted modification of the genome.

In addition to transgenic approaches, gene modification via homologous recombination is also possible. The nucleic acid sequence is initially assembled in a specifically designed gene targeting vector such that the sequence to be inserted is flanked at both sides with genomic segments of the target sequence that serve as homology regions to initiate homologous recombination. Typically, ES cells are then transfected with the gene targeting vector and recombinant ES cell clones are isolated and subsequently injected into blastocysts to transmit the mutant allele through the germ line of chimeras and to establish a mutant strain. (Hasty P, Abuin A, Bradley A., 2000, In Gene Targeting: a practical approach, ed. AL Joyner, pp. 1-35. Oxford: Oxford University Press; Nagy A, Gertsenstein M, Vintersten K, Behringer R., 2003. Manipulating the Mouse Embryo. Cold Spring Harbour, New York: Cold Spring Harbour Laboratory Press). In addition, recent approaches enable gene targeting via homologous recombination in oocytes by introducing into the oocyte a zinc finger- or TAL-nuclease together with the sequence to be inserted and flanking regions homologous to the target sequence (see e.g. WO 2011/051390 and WO 2011/154393).

To study gene function only in specific cell types or at specific developmental stages, conditional mutants may be generated.

Where the aim is conditional gene activation, as in the present case, the nucleic acid sequence encoding the gene to be activated (i.e. the one or more protein(s) that can be activated by light) comprises a further sequence, such as a gene encoding a resistance marker, flanked by two recombinase recognition sites (RRS) for a site-specific DNA recombinase. The presence of this additional sequence is arranged such that it prevents expression of the gene to be activated, for example by frame-shift or the presence of a polyadenylation signal. Recombination then results in the deletion of the RRS-flanked additional sequence, thus resulting in the expression of the gene to be activated in the cells/tissues expressing the recombinase.

Conditional mutants require the generation of two transgenic strains: one strain harboring an RRS flanked segment as described above, obtained by gene targeting in ES cells and a second, transgenic strain expressing the corresponding recombinase in one or several cell types. The conditional mutant is generated by crossing these two strains such that target gene inactivation or activation occurs in a spatial and temporal restricted manner, according to the pattern of recombinase expression in the second transgenic strain (Nagy A, Gertsenstein M, Vintersten K, Behringer R. 2003. Manipulating the Mouse Embryo, third edition ed. Cold Spring Harbour, New York: Cold Spring Harbour Laboratory Press; Torres RM, Kühn R. 1997. Laboratory protocols for conditional gene targeting. Oxford: Oxford University Press).

Gene trapping is a further approach that is used to achieve insertion of nucleic acid sequences of interest into pre-characterized loci in the genome of cells, as a high-throughput method. Exemplary gene trapping techniques that have been developed are based on the replacement of a cassette that was previously introduced into a gene locus, such as e.g. the recombinase mediated cassette exchange (RMCE) as described in Baer and Bode 2001 (J. Curr Opin Biotechnol. 2001; 12(5)) or Flp-RMCE as described in Cesari et al. 2004 (Genesis 2004; 38(2)) and the method as described in e.g. WO 2011/064262.

In addition, a powerful approach of introducing mutations into the genome is insertional mutagenesis mediated by transposons, which have become invaluable genomic tools in invertebrates and have also gained importance for mutagenesis in vertebrates, such as e.g. fish.

The term "transposon" refers to segments of DNA that can move (transpose) within the genome. Genes may not only be inactivated by transposon insertion, a transposon may also introduce a transgene of interest into the genome. Similarly to the methods described herein above, also transposons may carry regulatory elements necessary for the expression of the transgene, thus allowing for successful expression of said gene. Further, a transposon may or may not encode the enzyme transposase, necessary to catalyze its relocation and/or duplication in the genome. Where a transposon does not encode for its transposase enzyme, expression of said enzyme in-trans may be required in cells not expressing the relevant transposase itself. Furthermore, the transposon contains sequences that are required for its mobilization, namely the terminal inverted repeats containing the binding sites for the transposase.

Transposons can be derived from a bacterial or a eukaryotic transposon; and the transposon may be derived from a class I or class II transposon. Class II or DNA-mediated transposable elements are preferred for gene transfer applications, because transposition of these elements does not involve a reverse transcription step (involved in transposition of Class I or retroelements) which can introduce undesired mutations into transgenes (Miller, A. D., 1997, "Development and applications of retroviral vectors". Retroviruses: 843 (Cold Spring Harbor Laboratory Press, New York); Verma, I. M. and Somia, N., 1997, "Gene therapy? promises, problems and prospects". Nature 389:239).

Viral and non-viral technologies have been devised to facilitate the penetration of transgenes through biological membranes. When transposons are used in insertional mutagenesis screens, transposon vectors often comprise four major classes of constructs to identify the mutated genes rapidly. These contain a reporter gene, which should be expressed depending on the genetic context of the integration. In enhancer traps, the expression of the reporter requires the presence of a genomic cis-regulator to act on an attenuated promoter within the integrated construct. Promoter traps contain no promoter at all. These vectors are only expressed if they land in-frame in an exon or close downstream to a promoter of an expressed gene. In polyA traps, the marker gene lacks a polyA signal, but contains a splice donor (SD) site. Thus, when integrating into an intron, a fusion transcript can be synthesized comprising the marker and the downstream exons of the trapped gene. Gene traps (or exon traps) also lack promoters, but are equipped with a splice acceptor (SA) preceding the marker gene. Reporter activation occurs if the vector is integrated into an expressed gene, and splicing between the reporter and an upstream exon takes place. The gene trap and polyA trap cassettes can be combined. In that case, the marker of the polyA trap part is amended with a promoter so that the vector can also trap downstream exons, and both upstream and downstream fusion transcripts of the trapped gene can be obtained. The above constructs also offer the possibility to visualize spatial and temporal expression patterns of the mutated genes by using, e.g., LacZ or fluorescent proteins as a marker gene.

A milestone in the use of transposons in vertebrate genomics was the creation of the Sleeping Beauty (SB) element (Ivics, Z. et al., 1997: "Molecular reconstruction of Sleeping Beauty, a Tc1-like transposon from fish, and its transposition in human cells". Cell 91(4):501). Sleeping Beauty transposition is efficient in cells of different vertebrate classes (Izsvak, Z. et al., 2000: "Sleeping Beauty, a wide host-range transposon vector for genetic transformation in vertebrates". *J Mol Biol.* 302(1):93; Lu, B. et al., 2007: "Generation of rat mutants using a coat color-tagged Sleeping Beauty transposon system". *Mamm Genome* 18(5): 338; Luo, G. et al., 1998: "Chromosomal transposition of a Tc1/mariner-like element in mouse embryonic stem cells". *Proc Natl Acad Sci USA* 95(18):10769; Horie, K. et al., 2003: "Characterization of Sleeping Beauty transposition and its application to genetic screening in mice". *Mol Cell Biol* 23(24):9189). Further developments of the transoposon system for the site-specific targeting of desired polynucleotides into DNA sequences are described e.g. in WO 2004/070042, WO 2004/069995 and WO 2004/069994.

For the generation of transgenic zebrafish, a state-of-art method utilizes the transposon Tol2, isolated from the medaka system (Kawakami K. (2007)).

Preferably, the nucleic acid sequence(s) encoding the one or more protein(s) that can be activated by light is/are inserted into the genome of a recipient non-human vertebrate by homologous recombination or mutagenesis mediated by transposons.

The nucleic acid sequence encoding the one or more protein(s) that can be activated by light may be inserted into the genome of the recipient non-human vertebrate such that said nucleic acid sequence is under the control of endogenous regulatory sequences present in the genome of the non-human vertebrate. Alternatively, the nucleic acid sequence encoding the one or more protein(s) that can be activated by light may be inserted into the genome of the non-human vertebrate together with regulatory sequences required to ensure their expression. Preferably, the nucleic acid sequence encoding the one or more protein(s) that can be activated by light is operatively linked to such expression control sequences allowing expression in vertebrate cells. Such regulatory sequences are well known to those skilled in the art and include, without being limiting, regulatory sequences ensuring the initiation of transcription, internal ribosomal entry sites (IRES) (Owens, Proc. Natl. Acad. Sci. USA 98 (2001), 1471-1476), viral 2A peptide (Tang et al. J Neurosci. (2009) 29(27):8621-9) and optionally regulatory elements ensuring termination of transcription and stabilization of the transcript. Non-limiting examples for regulatory elements ensuring the initiation of transcription comprise a translation initiation codon, enhancers such as e.g. the SV40-enhancer, insulators and/or promoters, such as for example the cytomegalovirus (CMV) promoter, SV40-promoter, RSV-promoter (Rous sarcome virus), the lacZ promoter, the gai10 promoter, human elongation factor 1α-promoter, CMV enhancer, CaM-kinase promoter or the *autographa californica* multiple nuclear polyhedrosis virus (AcMNPV) polyhedral promoter. Particularly preferred promoter sequences in accordance with the present invention include promoters of genes expressed in cells of the hypothalamic-pituitary-adrenal axis, such as e.g. promoters involved in the expression of genes encoding stress-controlling hormones such as the promoters for corticotropin-releasing-hormon (CRH), arginine vasopressin (AVP), hypocretin (Hcrt) etc.; promoters of transcription factors that are expressed in the paraventricular nucleus of the hypothalamus, which is the major stress control region, such as e.g. orthopedia (Otp), single-mined 1 (Sim1), Nkx2, Fezf2, etc.; promoters of genes for specific expression in pituitary corticotroph cells (see e.g. Liu et al. Mol Endocrinol. 2003 May; 17(5):959-66); promoters of genes that are involved in steroidogenesis and are expressed specifically in the adrenal gland including steroidogenic factor 1 (SF1), cytochrome p450 side chain cleavage (P450scc), steoridogenic acute regulatory protein (StAR), and 3beta-hydroxysteroid dehydrogenase (3b-HSD); as well as e.g. the promoter of the ACTH receptor, also referred to as MC2R. Non-limiting examples for regulatory elements ensuring transcription termination include the V40-poly-A site, the tk-poly-A site or the SV40, lacZ or AcMNPV polyhedral polyadenylation signals, which are to be included downstream of the nucleic acid sequence encoding the one or more protein(s) that can be activated by light. Additional regulatory elements may include translational enhancers, nucleotide sequences encoding secretion signals or, depending on the expression system used, signal sequences capable of directing the expressed polypeptide to a cellular compartment. All of the above described sequences are well known in the art.

The nucleic acid sequence encoding the one or more protein(s) that can be activated by light may furthermore be inserted into the genome of the non-human vertebrate together with a selectable marker. Examples of selectable markers include markers providing resistance to neomycin, ampicillin, hygromycin and the like and are well known in the art.

The nucleic acid sequence encoding the one or more protein(s) that can be activated by light may be comprised in an expression vector that is capable of directing the replication, and the expression, of said nucleic acid sequences. Suitable expression vectors which comprise the above described regulatory elements are known in the art such as Okayama-Berg cDNA expression vector pcDV1 (Pharmacia), pRc/CMV, pcDNA1, pcDNA3 (Invitrogen), pSPORT1 (GIBCO BRL), Gateway plasmids (Invitrogen) or pGEMHE (Promega). For transgenesis in zebrafish, the nucleic acid sequences can for example be expressed using vectors in the Toll kit as described in the art, e.g. in Kwan et al. (Dev Dyn. 2007 November; 236(11):3088-99).

The nucleic acid sequences for generation of the genetically modified non-human vertebrate may be designed for direct introduction, such as e.g. injection, or for introduction via electroporation (using for example Multiporator (Eppendorf) or Genepulser (BioRad)), PEI (Polysciences Inc. Warrington, Eppelheim), $Ca^{2+}$-mediated transfection or via liposomes (for example: "Lipofectamine" (Invitrogen)), non-liposomal compounds (for example: "Fugene" (Roche)), liposomes, phage vectors or viral vectors (e.g. adenoviral, retroviral, lentiviral) into cells. Additionally, baculoviral systems or systems based on Vaccinia Virus or Semliki Forest Virus can also be used.

Nucleic acid sequences, in accordance with the present invention, include DNA, such as cDNA or genomic DNA including exonic and intronic sequences, and RNA, preferably mRNA.

Preferably, the nucleic acid sequence encoding the one or more protein(s) that can be activated by light is cDNA.

Protein(s) that can be activated by light, also referred to interchangeably herein as light-activatable proteins or light-activated proteins, are proteins whose function is activated by exposure to light. Non-limiting examples of light-activated proteins include microbial opsins, light-gated channels and photo-activated adenylyl cyclase. Microbial opsins, such as e.g. channelrhodopsin and halorhodopsin, have been successfully used in larval zebrafish to trigger escape reactions (Douglass et al., 2008), control cardiac function (Arrenberg et al., 2010), identify distinct groups of neurons controlling swimming (Arrenberg et al., 2009), and targeted manipulations of neurons responsible for eye movements (Schoonheim et al., 2010). Channelrhodopsins and halorhodopsins are light-gated ion channels that allow neuronal depolarization/hyperpolarization upon light activation with absorption maximum at 480nm and 570 nm, respectively.

A light gated channel (LiGluR), expressed in spinal cord neurons, has been reported to induce tail beatings (Wyart et al., 2009). LiGluR is a genetically encoded glutamate channel which opens in a light-regulatable fashion which opens and closes upon the reversible photoisomerization at 500 nm and 380 nm, respectively.

Alongside membrane voltage modulators, another class of light-activated proteins modulating the ubiquitous second messenger molecule cyclic adenosine monophosphate (cAMP) has also been reported. The light-activated adenylyl cyclase (PACα) is central to photo-avoidance in the unicellular flagellate *Euglena gracilis*. This enzyme contains BLUF-type photoreceptor domains (sensors of blue light using flavin adenine dinucleotide) that make it sensitive to blue light (Iseki et al. 2002). Expression of the PACα sub-unit increases cAMP levels in HEK293 cells following photo activation. Moreover, light induced increase in cAMP was shown to be sufficient to trigger intracellular pathways. This was shown in *Xenopus oocytes* by a light induced increase in plasma membrane conductance caused by a $Cl^-$-channel, which is dependent on activation by PKA (cAMP dependent protein kinase A) (Schroder-Lang et al., 2007). PACα has been reported to modulate hyperactivity, freezing and grooming in *Drosophila* (Schroder-Lang et al., 2007), as well as locomotor activity in *Caenorhabditis elegans* (Weissenberger et al., 2011). Moreover, a novel PAC from the bacterium Beggiatoa (bPAC) with lower dark activity, higher in-light activity and a smaller size than PACα has recently been reported and successfully used in *E. coli, Xenopus oocytes* and *Drosophila* (Stierl et al., 2011). bPAC is activatable at a wavelength of 450 nm.

Exposure to light in order to activate said proteins can be achieved by means well known in the art. For example, due to the size and transparency of their body, larval zebrafish or medaka may simply be exposed to light, preferably at the respective wavelength as indicated above, in order to activate the light-activated proteins. Alternatively, where larger and non-transparent animals such as e.g. mice or rats are employed, the implantation of optical fibers in the vicinity of the cells expressing the light-activated protein can be carried out by methods well known in the art, e.g. in Wang et al. 2011 or Anikeeva et al. 2011.

Cells of the hypothalamic-pituitary-adrenal axis, in accordance with the present invention, include neuroendocrine cells in the paraventricular nucleus (PVN) of the rostral hypothalamus, corticotroph cells in the anterior pituitary and steroidogenic cells in the adrenal cortex.

The protein(s) that can be activated by light are capable of inducing the release of specific hormones and glucocorticoids, as detailed herein below. Inducing the release, in this context, includes both the induction of release of existing hormones and/or glucocorticoids from cells as well as the induction of the expression or formation and release of said new formed hormones and/or glucocorticoids. In other words, the light-activated proteins can either induce the release or can induce the biosynthesis and subsequent release of said hormones and/or glucocorticoids.

In accordance with the present invention, the light-activated proteins induce the release of (i) corticotrophin-releasing hormone (CRH) and/or arginine-vasopressin (AVP) from neurons in the paraventricular nucleus of the rostral hypothalamus; and/or (ii) adrenocorticotropic hormone (ACTH) from corticotroph cells in the anterior pituitary; and/or (iii) glucocorticoids from cells in the adrenal cortex. With regard to the release of CRH and/or AVP from neurons in the paraventricular nucleus of the rostral hypothalamus, release of one of these two hormones is sufficient to mediate a stress response but induction of the release of both hormones is also contemplated, and preferred, in accordance with the present invention. The glucocorticoids that can be released from cells of the adrenal cortex include e.g. cortisol in humans and in fish and corticosterone in rodents.

The skilled person is aware of how to choose a suitable light-activated protein in order to successfully induce the release of the respective hormone or glucocorticoid. For example, and as shown in the appended Examples below, light-activated adenylate cyclase (PAC), such as e.g. beggiatoa photoactivated adenylyl cyclase (bPAC), can be expressed specifically in pituitary cells using the promoter of the pomc gene, which encodes the precursor of ACTH.

This approach ensures the generation of cAMP in the pituitary cells expressing PAC, which in turn is central to CRH receptor signal transduction within these pituitary cells, ultimately resulting in an increase of cortisol levels in the animal model. In more detail, an increase in cAMP in corticotrophs leads to an influx of $Ca^{2+}$ and a concomitant $Ca^{2+}$-mediated ACTH release. cAMP signaling is important for many hormone release processes and therefore PAC can also be expressed in the hypothalamic neuroendocrine cells to enhance CRH/AVP release.

In accordance with the present invention, a model for the precise and non-invasive detection and control of stress response has been developed. The model entails the expression of light-activated proteins, such as e.g. channels and enzymes, specifically in stress hormone producing neurons using cell-type specific promoters to induce stress responses. Thus, optical control of specific neuronal populations in freely moving subjects is achieved.

In vertebrates, the stress response is regulated by the activation of highly conserved neuroendocrine cells in the hypothalamus producing stress hormones such as corticotropin-releasing hormone (CRH) (Charmandari et al. (2005)). Once produced, CRH activates pituitary corticotrophs to release adrenocorticotropic hormone (ACTH) via G-protein coupled receptors and subsequent cAMP-mediated signaling (Arzt and Holsboer (2006)).

As a proof of principle, zebrafish were used herein as a model system and a transgenic line was generated that expresses light-gated adenylate cyclase (PAC) specifically in pituitary cells using the promoter of the pomc gene, which encodes the precursor of ACTH. In this animal, upon blue-light illumination, a dose-dependent increase in the level of a stress hormone, cortisol, was achieved. Further, using light, the stress behavior of zebrafish larvae can be controlled and studied. The present application thus provides a novel animal model for (1) investigating stress behavior, such as e.g. chronic stress; (2) screening for novel regulators of stress response, (3) manipulating the stress level during development to achieve early life stress animal model, (4) controlling stress behavior both acutely and chronically in animal models and (5) testing of drugs that target the stress response system. In summary, this system allows a direct, non-invasive, quantitative and precise detection and manipulation of the stress response in vertebrates.

In a preferred embodiment of the method of the invention, the protein(s) that can be activated by light is/are selected from the group consisting of light-activated adenylate cyclase (PAC), channelrhodopsin 1 and channelrhodopsin 2.

Light-activated adenylate cyclase and its amino acid sequence as well as the nucleic acid sequence encoding said protein have been described in e.g. Stierl et al. 2011. Also channelrhodopsin 1 and channelrhodopsin 2 have been described in the art, e.g. in Nagel et al. 2002.

In another preferred embodiment of the method of the invention, the non-human vertebrate is a fish.

In recent decades, fish have emerged as a promising vertebrate model organism for biomedical research. They can easily be handled in the laboratory and have a fast generation time and large reproductive clutches. Thus, they offer an excellent model for the analysis of such interactions, in particular as their HPI-axis is homologous to the HPA axis in humans.

The endocrinological measurements required to analyse stress responses in larger animal models such as e.g. rodents that are currently employed in the art are typically labor-intensive and are often not standardized between different laboratories. Thus, the use of a smaller vertebrate model, such as fish, provides a set of read-outs and precise manipulation protocols that are easily scalable in multi-well formats for a high through put screen and analysis.

In an even more preferred embodiment, the fish is selected from zebrafish and medaka.

Zebrafish, *Danio rerio*, is a freshwater teleost natively found in rivers and streams near rice paddies in India and neighboring countries (Engeszer et al., 2007). One particular advantage of zebrafish is that their stress response system shares fundamental similarities with that of mammalian research models (Wendelaar Bonga, 1997, Alsop and Vijayan, 2009). By the time of hatching, larval zebrafish develop a functional HPI-axis, and by day four, their whole-body cortisol level increases rapidly in response to stressors (To et al., 2007, Alsop and Vijayan, 2008, Alderman and Bernier, 2009). Mechanosensory stimulation and various chemicals and pollutants can be used as stressors, and can easily be applied to the aqueous environment of zebrafish. Moreover, because zebrafish are poikilothermic and stenohaline, temperature and salinity changes can also be used as distinct stressors suitable for the analysis of stress response function.

Of importance is that the oviparous development of zebrafish, the small size and transparent body of its larvae and the available repertoire of tools for both selective targeting of cell stress pathways and non-invasive brain imaging and optogenetic probing of neuronal circuitry provide an excellent opportunity to study the development of the stress axis and a fully functional stress response.

Similar to zebrafish, medaka also offers an advantage as a small vertebrate model with fully sequenced genome and translucence larvae suitable for optical manipulations.

The present invention further relates to an animal model of stress obtained by the method of the invention.

Furthermore, the present invention also relates to the use of an animal model in accordance with the invention for screening for a compound for preventing, ameliorating or treating stress and/or stress-associated diseases.

Essentially any compound can be assayed for its potential to prevent, ameliorate or treat stress and/or stress-associated diseases in accordance with the present invention. Such compounds include e.g. small molecules, such as organic or inorganic molecules. Organic molecules relate or belong to the class of chemical compounds having a carbon basis, the carbon atoms linked together by carbon-carbon bonds, including biological entities such as e.g. proteins, sugars, nucleic acids, lipids. The original definition of the term organic related to the source of chemical compounds, with organic compounds being those carbon-containing compounds obtained from plant or animal or microbial sources. Organic compounds can be natural or synthetic. Small organic molecules preferably have a molecular weight of about 500 Da or below. Inorganic compounds are derived from mineral sources and include all compounds without carbon atoms (except carbon dioxide, carbon monoxide and carbonates). There are many suppliers of such compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. In addition, compounds to be analysed may be synthesized by methods known in the art. Test compounds may be comprised in compound libraries of diverse or structurally similar compounds (e.g, combinatorial chemistry synthesized libraries) and a plurality of test compounds in a library can be assayed simultaneously. Optionally, test compounds derived from different libraries can be pooled for simultaneous evaluation. A library can comprise a random collection of molecules. Alternatively, a library can comprise a collection of molecules having a bias for a particular sequence, structure, or conformation. Methods for preparing libraries containing diverse populations of various types of molecules are known in the art (Brenk, R. et al., Lessons Learnt from Assembling Screening Libraries for Drug Discovery for Neglected Diseases, ChemMedChem 2008, 3, 435-444, Quinn J. R. et al., Developing a Drug-like Natural Product Library, J. Nat. Prod. 2008, 71, 464-468). Numerous libraries are also commercially available.

Preferred compounds for screening for their potential in preventing, ameliorating or treating stress and/or stress-associated diseases include, without being limiting, antidepressants, such as e.g. fluoxetine, due to the strong connection between stress and depression (Holsboer and (sing 2010; Holsboer et al. 1984) or tranquilizers, such as diazepam.

The term "stress-associated diseases", in accordance with the present invention, relates to conditions that develop as a consequence of acute or chronic stress within the subject. Non-limiting examples of such stress-associated diseases are heart disease, chronic fatigue, anxiety attacks, mood swings, psychological distress, depression, sleep problems, high blood pressure, eating disorders, peptic ulcers, poor immune function, chronic pain, colds, flu, virus infections, alcoholism, headaches and migraines.

The present invention further relates to a method of screening for a compound for preventing, ameliorating and/or treating stress and/or stress-associated diseases, the method comprising (a) administering a test compound to an animal model of the invention; (b) inducing stress in said animal model prior to step (a), simultaneously with step (a) or after step (a); and (c) analysing the stress response induced in step (b), wherein a reduced stress response observed in (c) in the presence of the test compound as compared to the stress response observed in the absence of the test compound is indicative of a compound suitable as a compound for preventing, ameliorating and/or treating stress and/or stress-associated diseases.

All definitions and preferred embodiments provided herein with regard to the method of producing an inducible animal model of stress and the use of such an animal model apply mutatis mutandis also to this screening method of the invention.

In accordance with this method of the invention, a compound to be tested is administered to an animal model of the invention in a first step. Methods of administering a test compound are well known in the art and include e.g. parenteral, rectal, oral, intracisternal, intravenous, intraperitoneal, subcutaneous, intramuscular, intradermal, topical (e.g. as powders, ointments, drops or transdermal patch), intranasal, buccal, nasal or intrabronchial administration. Moreover, the compound may be administered into the environment surrounding the animal model, e.g. into the water in case of fish or into the air in the case of other vertebrates such as laboratory rodents, e.g. mice or rats.

Stress is induced in said animal model either prior to the administration of the test compound in step (a), simultaneously with the administration of the test compound in step (a) and/or after the administration of the test compound in step (a). In a preferred embodiment of this method of the invention, the stress is induced by exposing said animal to light. More preferably, inducing stress in the animal model of the present invention is achieved by exposing the animal model to a light stimulus of a specific wavelength. Variations in stress induction can be achieved by varying the light stimuli applied, e.g. using multiple, repeated light stimuli or a single long exposure of light etc.

After the induction of stress, the stress response thus induced in the animal model is analysed. Such analysis encompasses behavioral tests, such as e.g. tail-suspension, water-maze, open-field, light/dark box choice, elevated plus-maze etc., all of which are well known in the art and described e.g. in Prut and Belzung (2003) or Belzung and Griebel (2001), or any of the tests described herein below and in the appended Examples.

The stress response observed in the presence of the test compound can then be compared to the stress response observed in the absence of the test compound. In those cases where a reduced stress response is observed in the presence of the test compound as compared to the stress response observed in the absence of the test compound, the compound is suitable as a compound for preventing, ameliorating and/or treating stress and/or stress-associated diseases or as a lead compound for the development of a compound for preventing, ameliorating and/or treating stress and/or stress-associated diseases.

In a preferred embodiment of the methods, the animal or the use of the invention, the stress is chronic stress.

In accordance with the present invention, chronic stress is defined by a long-lasting alteration of stress behavior and altered level of stress hormones. Chronic stress results in a characteristic dysregulation of the HPA axis and enhances vulnerability to a variety of disease including depression (see e.g. Chrousos and Gold (1992)). Both chronically elevated glucocorticoid levels and increased central CRH levels are implicated in depression-associated HPA hyperactivity (Holsboer 1999; Holsboer and Barden 1996; Raadsheer et al. 1994) and, therefore, persistent elevation of the level of both of these hormones at the protein or at the DNA can be used as an indicated of chronic stress.

Methods for determining the expression of these hormones on the nucleic acid level include, but are not limited to, northern blotting, PCR, qPCR, RT-PCR or real time RT-PCR. Methods for the determination of the expression of these hormones on the amino acid level include but are not limited to ELISA, western blotting or polyacrylamide gel electrophoresis in conjunction with protein staining techniques such as Coomassie Brilliant blue or silver-staining. Also of use in protein quantification is the Agilent Bioanalyzer technique. These methods are well known in the art.

Furthermore, the present invention relates to a method of analyzing stress behavior in fish, the method comprising (i) placing a fish in a swimming chamber and exposing the fish to a stimulus; and (ii) analyzing the stimulus-dependent behavior of the fish in the presence or absence of a stressor; wherein an alteration of behavior observed in (ii) in the presence of a stressor as compared to the behavior observed in (ii) in the absence of a stressor is indicative of stress.

Although reference is made in accordance with the methods of the present invention to "a fish", also the use of a plurality of fish is envisaged herein and is, thus, encompassed by the term "a fish". Moreover, the term "fish" as used herein relates to both larval (i.e. the juvenile, non-adult) fish as well as adult fish. Preferably, the fish is a larval fish.

The swimming chamber may be any swimming chamber commonly employed in the art, such as a single-compartment or a multiple-compartment swimming chamber. It will be appreciated that when using multiple-compartment swimming chambers, said compartments are interconnected with each other.

The fish is then exposed to a stimulus, which can be any stimulus of interest, such as the below described preferred stimuli. The behavior of the fish after exposure to the stimulus (i.e. the "stimulus-dependent behavior", also referred to herein as "the behavior in response to the stimulus") is monitored and is compared to its behavior in the presence of a stressor. An altered behavior in response to the stimulus, such as a change in movement (e.g. distance moved per unit time (locomotion level)), space utilization (e.g. proportion of time spend in certain compartments or sections of the chamber), feeding motivation etc. after exposure to the stressor as compared to the behavior in response to the stimulus prior to exposure to the stressor is indicative of stress. Thus, the change in a particular stimulus-dependent behavior is employed as an output to evaluate the effect a particular stressor has on the fish. This stress response can be quantified with regard to the stimulus.

The stressor may be any stressor of interested, such as e.g. osmotic changes, mechanosensory perturbations or light-activated stress induction in accordance with the animal model of the present invention.

The term "monitoring", as used herein, refers to any kind of observation of the behavior of the fish for changes which may occur over time, using a monitor or measuring device of some sort or by simple observation and recording by a researcher. For example, a video camera can be employed to record the behavior of the fish and suitable analysis software may be employed to determine the respective behavioral features, such as distance travelled, space used etc.

In accordance with the present invention, novel behavioral assays in fish as read-outs for normal and altered stress-response detection are provided. To detect stress-dependent changes in behavior, several novel behavioral assays were developed, which include measuring 1) responsiveness to temperature change, 2) responsiveness to illumination change, 3) responsiveness to subtle mechanical perturbation of the surrounding medium, and 4) feeding motivation.

The Input-Output relationship using defined external stimuli and the corresponding behavioral output serve as the main readouts for stress in accordance with the present invention. Stress influences behavior in multiple ways, ranging from immediate changes in locomotion to alterations in arousal, feeding, learning and memory. In particular, it can modify an organism's control properties so as to alter (increase or decrease) its responsiveness to external stimuli to effectively avoid threats. While visually-guided behaviors have been well characterized in zebrafish, other behavioral paradigms are scant. Therefore larval zebrafish response to two independent sensory stimuli, namely mechanical and temperature stimuli, was characterized in accordance with the present invention. To the inventor's best knowledge, these behaviors have not been described in the literature and represent novel behavioral paradigms that can be precisely quantified and controlled. Moreover, it was not known so far that responsiveness of larval zebrafish to photic stimuli represents a stress behavior, which is a further novel finding in accordance with the present invention. Hence, response to photic stimuli constitutes a further stress behavior which can be enhanced by optogenetic manipulation of the HPA axis.

Accordingly, in a preferred embodiment of this method of analyzing stress behavior in fish, the stimulus is selected from temperature change, illumination change or mechanosensory stimulation.

As is shown in Example 2 below, temperature changes, subtle mechanosensory stimulation as well as illumination change was used as the source of external stimulation for larval zebrafish. The reaction of the fish to said stimuli was used as a measure of stress responsiveness.

In another preferred embodiment of this method of the invention, the stimulus is food. Accordingly, in a more preferred embodiment the step of analyzing the behavior of the fish comprises determining the feeding motivation of the fish, wherein the feeding motivation is analysed by (a) placing a fish in a swimming chamber; and (b) analyzing the movement of the fish after addition of food; wherein a differential spatial use within the swimming chamber towards the compartment(s) comprising the food is indicative of a feeding motivation of said fish.

In accordance with this embodiment of the invention, the feeding motivation of fish is used as a read-out for the level of stress the fish is experiencing. The term "feeding motivation", as used herein, relates to the drive of a fish, to obtain and take up food. To this end, the fish is placed in a swimming chamber and its movement, i.e. the spatial use of the available room within said swimming chamber (proportion of time spend in certain compartments or sections of the chamber) as well as distance moved per unit time (locomotion level) are monitored. By monitoring the fish's movement both in the absence of food as well as in the presence of food, a comparison can be carried out. The change in time spent in those parts of the chamber containing the food and/or a change in locomotion level upon addition of food represents a quantifiable measure of the feeding behavior of the fish.

As detailed herein above, the swimming chamber may be any swimming chamber commonly employed in the art. Where the swimming chamber comprises only a single compartment, the addition of food is carried out at a specific location, such as e.g. within one corner of the chamber, in order to generate an area comprising food while other areas of the swimming chamber remain devoid or substantially devoid of food. In those cases where the swimming chamber comprises a plurality of compartments, the addition of food is carried out such that at least one of the compartments contains food and at least one of the compartments is devoid or substantially devoid of food. Preferably, the swimming chamber comprises at least two interconnected compartments. Employing a swimming chamber with several compartments that are interconnected provides the advantage that alteration carried out in one compartment, such as e.g. addition of food or changes in the environment (temperature, osmolarity etc.) can be kept separate from the other compartment(s). Nonetheless, as the compartments are interconnected, the fish are free to use the entire available space. Moreover, the use of different compartments allows for an easy and correct quantification of % side bias of one compartment over the other compartment(s), which is not possible in a single compartment.

The term "substantially devoid of food" refers to an environment in which only minimal traces of food are present, for example due to diffusion from the area comprising the food. Preferably, the area or compartment substantially devoid of food comprises less than 10% of food as compared to the area comprising the food, such as e.g. less than 5%, less than 4%, less than 3%, less than 2% and more preferably less than 1%. Even more preferably, the area or compartment substantially devoid of food comprises less than 0.5% of food as compared to the area comprising the food and most preferably, less than 0.1% of food.

Suitable food for use in accordance with the present invention is well known in the art and includes, without being limiting, paramecia, artemia, amino acids or dry flakes.

In accordance with the present invention, the feeding motivation may be employed to analyze the stress response of a fish to a stressor. Accordingly, the method of analyzing stress behavior in fish in accordance with the present invention can be carried out by (i) placing a fish in a swimming chamber and exposing the fish to a stressor; and (ii) analyzing the feeding motivation of the fish after exposure to the stressor; wherein an altered feeding motivation after exposure to the stressor as compared to the feeding motivation prior to exposure to the stressor is indicative of stress.

As is shown in the appended example, a behavioral assays has been developed specially designed to estimate the motivation to feed of fish, and the effects of stressors on feeding motivation was measured. Thus, a reversible impairment of feeding motivation after stressor exposure was surprisingly observed, indicating that the analysis of feeding motivation is a suitable output for determining stress responses in fish.

In an alternative embodiment of the methods of analyzing stress behavior in fish, the method is an active avoidance test.

Active avoidance is well known in the art and refers to an animal behavior where the animal actively turns away from the stimulus, thereby escaping its effects. Non-limiting examples include the measurement of an animal's movement away from a source of increased temperature, as e.g. shown in Example 2 below, as well as from a sudden change in illumination or mechanical perturbations. Active avoidance is monitored as a change in spatial use of a freely moving animal, here a fish, upon exposure to a stimulus. A reduced usage of the space where the stimulus was applied represents an active avoidance of said stimulus.

In another preferred embodiment of the methods of analyzing stress behavior in fish, the fish is selected from zebrafish and medaka.

In yet another preferred embodiment of the methods of analyzing stress behavior in fish, the fish is an animal model of stress obtained by the method of the present invention.

As is shown in Example 2 below, optogenetically modified larval zebrafish were employed in stress behavior tests based on temperature change, mechanosensory stimulation or illumination change as the source of external stimulation of. From these data it can be concluded that a rise in cortisol levels (as induced by light induction of bPAC activity in the bPAC-positive transgenic larvae) can modify the responsiveness of larval zebrafish to external stimuli by shifting threshold response levels.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The figures show:

FIG. 1 Optogenetic approach to modify the gain of the stress axis using blue-light as a stressor. (a) Larval zebrafish swimming in darkness display stable rates of discontinuous motion (overall mean±S.E.M. shown as dotted line and grey background, respectively). (b) Exposing dark-adapted larvae to blue-light causes a decrease in motion followed by increased locomotion after the light-offset. (c) Blue-light also leads to increased cortisol level (Mann-Whitney test, $p<0.01$; sample size in parenthesis). (d) Targeted expression of beggiatoa photoactivated adenylyl cyclase (bPAC) to pituitary corticotrophs, which produce and release ACTH via intracellular cAMP signaling; CRHR, CRH-receptor; AC, adenelyl cyclase; PKA, protein kinase A; POMC, propiomelanocortin. (e) It was hypothesized that blue-light will lead to HPI-axis activation and enhanced cortisol level in bPAC-positive larvae. (f) Dorsal and lateral views of bPAC expression in two cell clusters in the pituitary of 6 days post fertilization (dpf) larvae, as detected by tdTomato fluorescence; enlarged images show co-expression of ACTH and fluorescent tdTomato signal. (g) Exposure to blue-light leads to higher cortisol levels in the bPAC-positive larvae (bPAC$^+$), as compared to their negative siblings (bPAC$^-$) (Two-way ANOVA, light power: $F_{(3,82)}=29.48$, $p<0.0001$; genotype: $F_{(1,82)}=23.09$, $p<0.0001$; light power X genotype: $F_{(3,82)}=1.77$, $p=0.16$; Bonferroni post-test s, $p<0.01$; letters, $p<0.05$, and asterisks, *$p<0.05$, **$p<0.01$, designate within- and between-group differences, respectively; sample size in parenthesis). (h) Locomotor activity as a function of time in bPAC$^+$ and bPAC$^-$ larvae after a 180s exposure to blue-light of 2.8 mW*cm$^{-2}$; the insert shows the ensuing 'area under the curve' values (mean±S.E.M.) (Mann-Whitney test, $p=0.02$; sample size in parenthesis).

Figure 2:
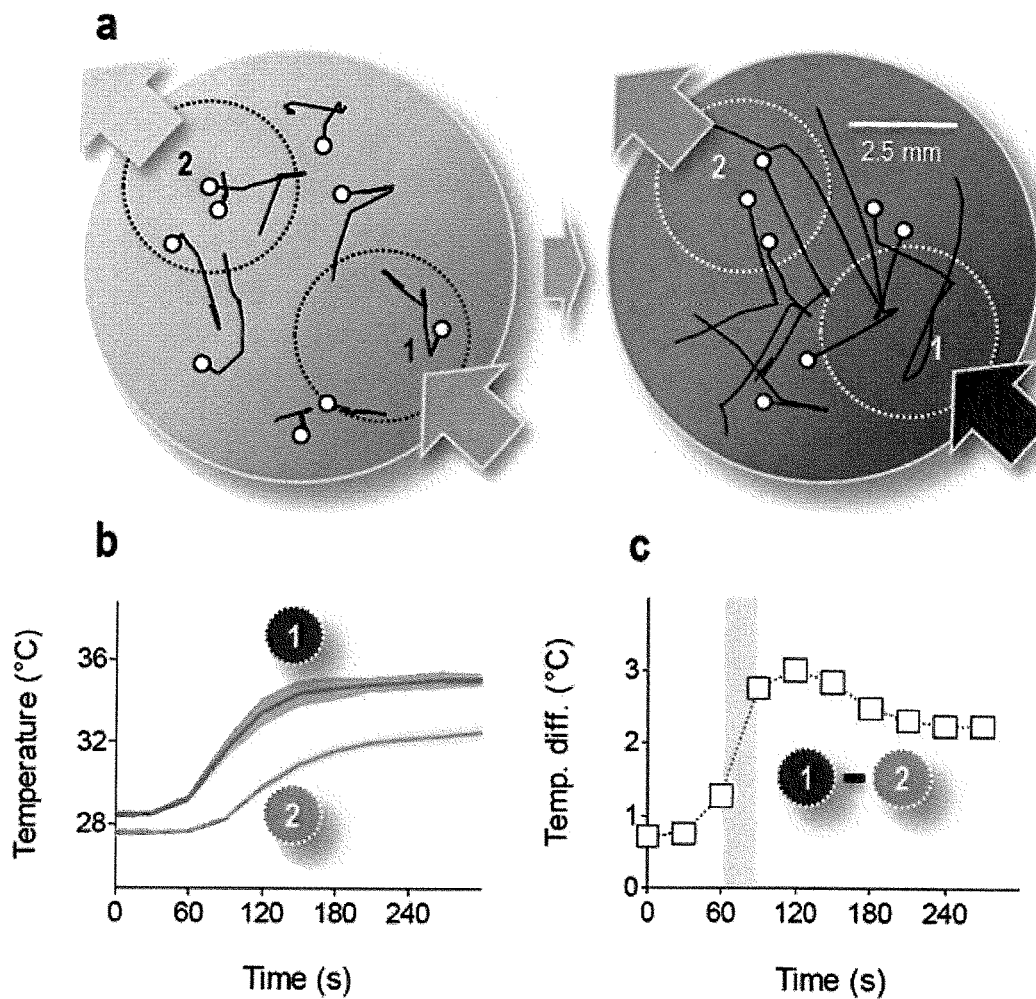
Figure 2:
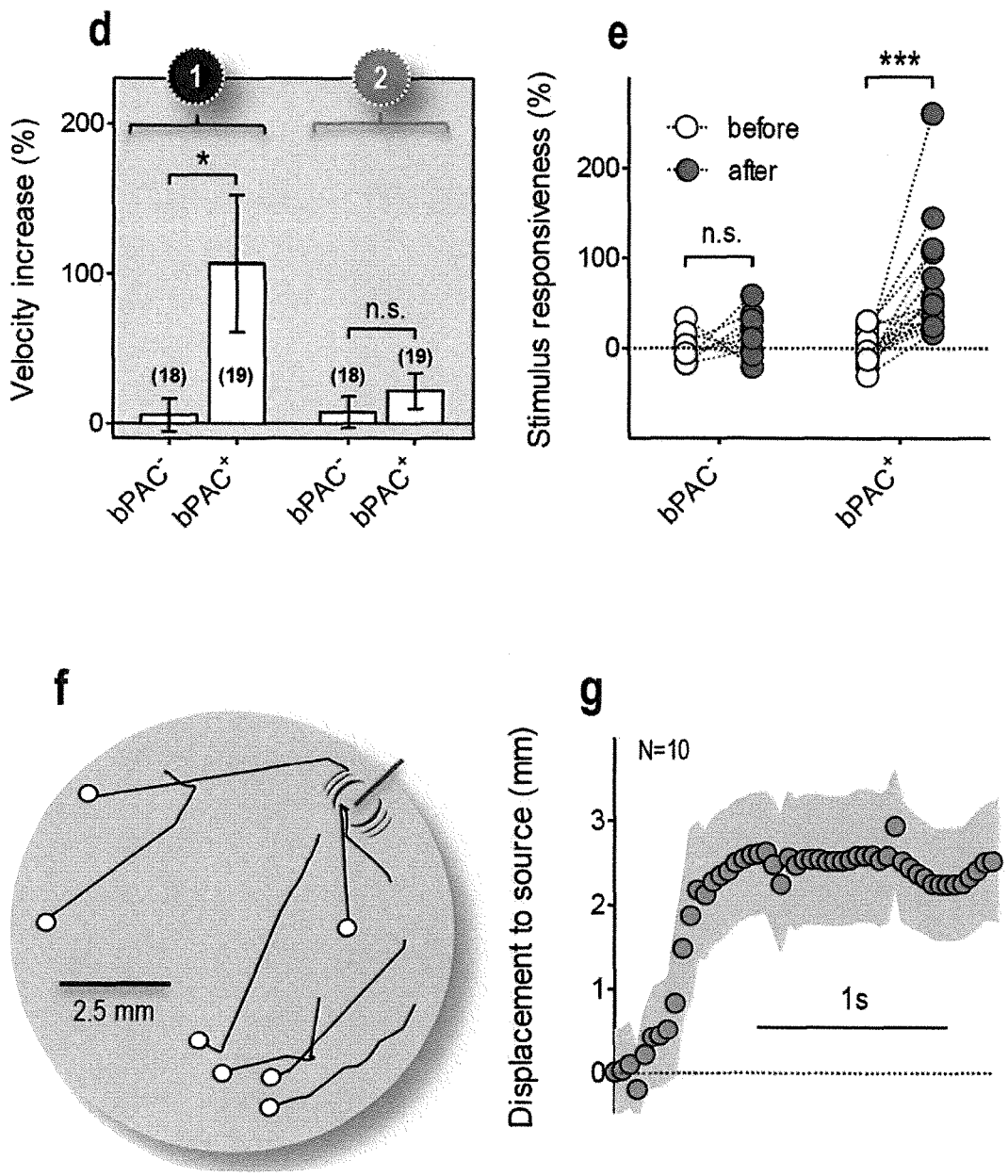
Figure 2:
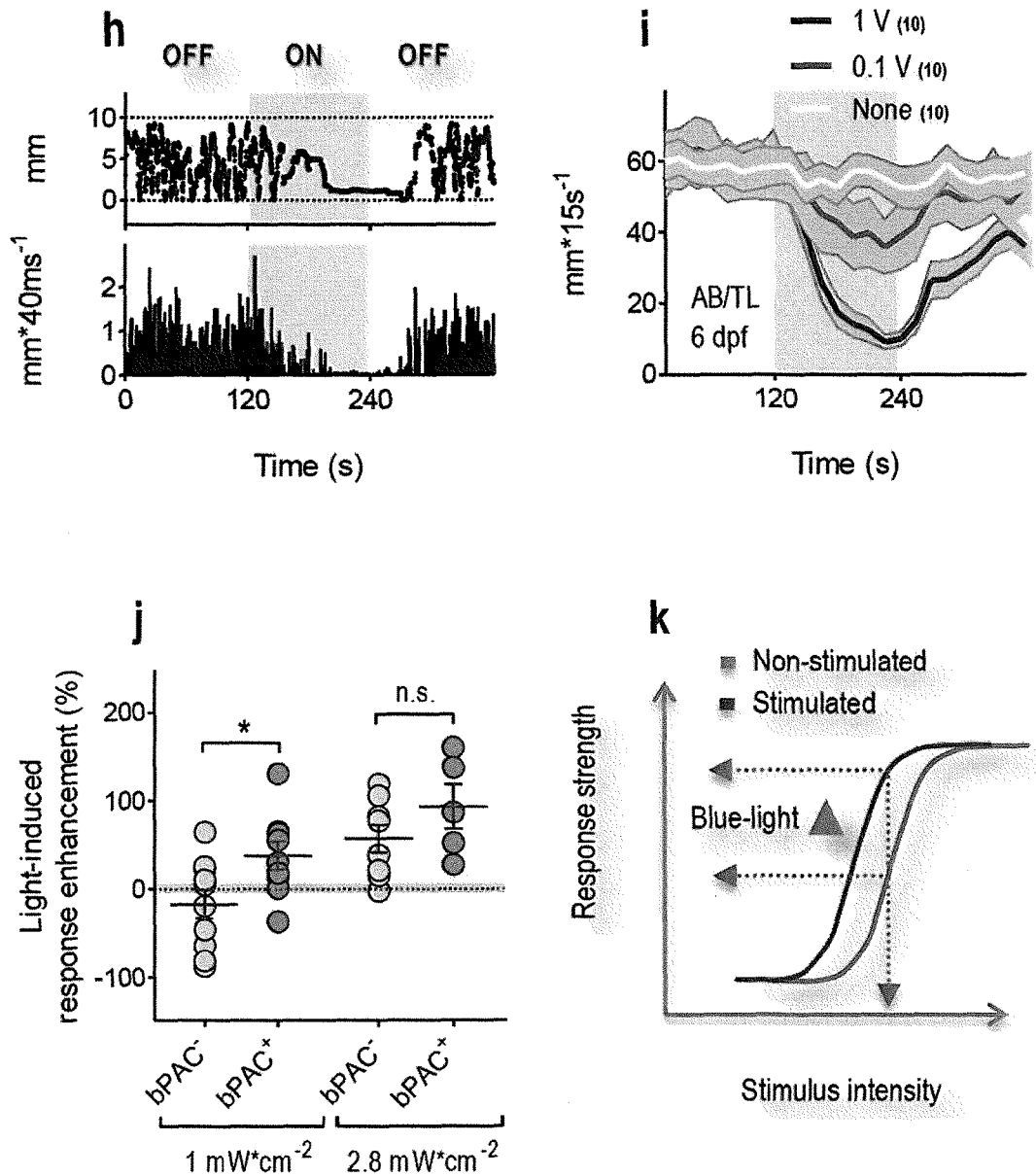

FIG. 2 Optogenetically enhanced glucocorticoid level improves stimulus responsiveness. (a) Increasing the temperature of the medium flowing into a small swimming chamber (right bottom arrows) raises not only the average temperature within the chamber (higher temperatures depicted as increasing red) but also the temperature difference between the zones 1 (high temp.) and 2 (low temp.), near the inlet and outlet, respectively; plotted are exemplary 1s swim paths showing increased speed and fast turns near zone 1 as temperature rises; white dots designate the larvae's starting positions. (b)

Average temperature in zones 1 and 2 (dark- and light-red lines, respectively) as a function of time. (c) Temperature difference between the zones as a function of time; note the rapid increase occurring 60-90s after the onset of temperature rise (set at zero). (d) Velocity increase (%) in bPAC$^+$ and bPAC$^-$ larvae 60-90s after the onset of temperature rise (Mann-Whitney test, p=0.01 and p=0.40 for positive versus negative larvae in zone 1 and 2, respectively). (e) Stimulus responsiveness in bPAC$^+$ and bPAC$^-$ larvae (Wilcoxon matched-pairs signed rank test, p=0.0006 for bPAC$^+$ larvae; t test, $t_{(8)}$=1.11, p=0.30 for bPAC$^-$ larvae). None-exposed bPAC$^+$ and bPAC$^-$ larvae do not respond differently to temperature change—not shown. (f) Larval zebrafish respond to a single 20 ms-long SMS unit by approaching the stimulation source; shown are exemplary 1s swim paths following SMS, the white dots and red line designate the larvae's starting positions and the source's location, respectively. (g) Average displacement to the stimulation source upon SMS. (h) Exemplary tracks depicting the distance to the stimulation source (top) and swimming velocity (bottom) as a function of time; pink backgrounds indicate repeated SMS (applied at 1 Hz for 120s). (i) The larvae's response to SMS is graded, as motion decrease magnitude increases with stimulus intensity. (j) Exposure to low intensity blue-light enhances responsiveness to SMS in bPAC$^+$ larvae only, whereas a higher light-intensity enhances SMS-responsiveness in both groups of larvae (Two-way ANOVA, light power: $F_{(1,28)}$=12.73, p=0.0013; genotype: $F_{(1,28)}$=6.28, p=0.018; light power X genotype: $F_{(1,28)}$=0.28, p=0.60; Bonferroni post-test s, *p<0.05; exposure time: 180s); zero corresponds to the mean response strength (±S.E.M., in grey) of non-exposed larvae. (k) Hypothetical effect of blue-light exposure on a larva's threshold level of response.

Figure 3:
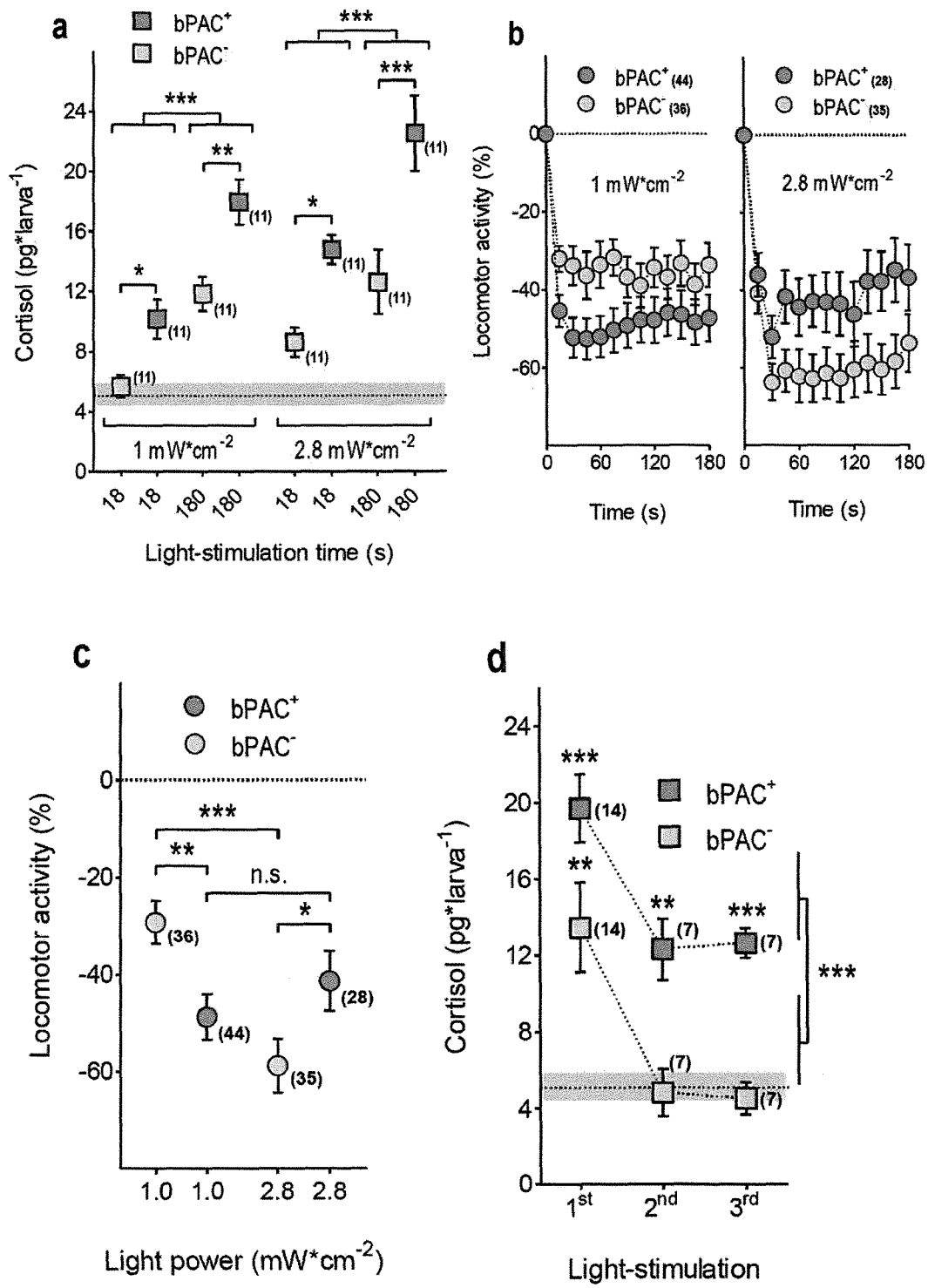
Figure 3:
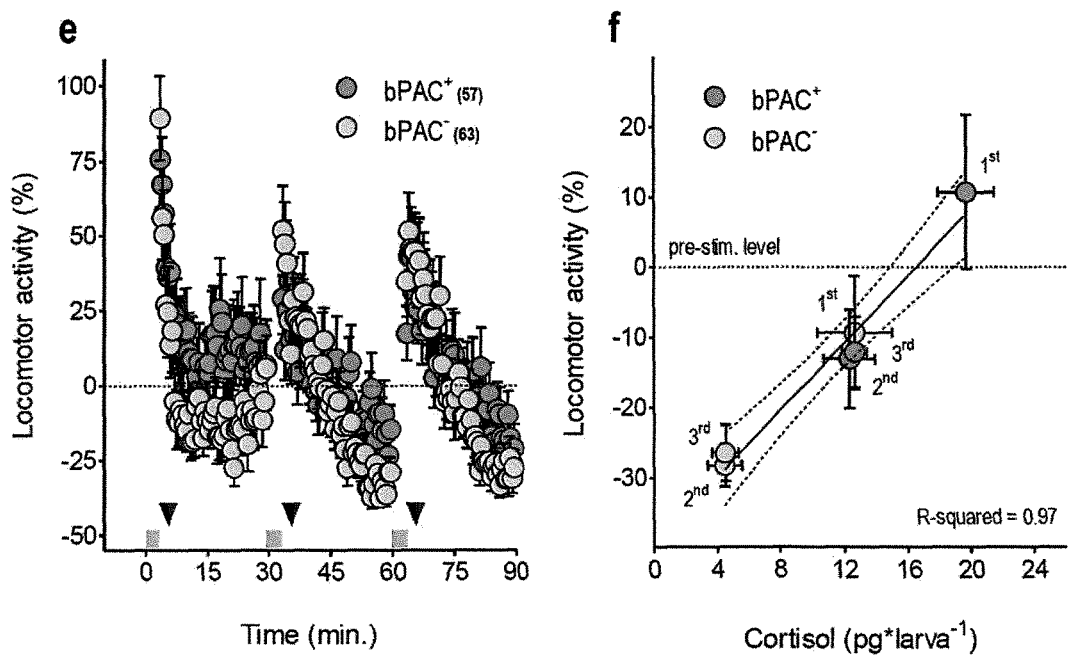

FIG. 3 Optogenetically induced correlated variations in glucocorticoid level and locomotor activity. (a) Cortisol level in bPAC$^+$ and bPAC$^-$ larvae as a function of exposure time and light-intensity (Two-Way ANOVA, left, length: $F_{(1,40)}$=33.85, p<0.0001; genotype: $F_{(1,40)}$=19.56, p<0.0001; length X genotype: $F_{(1,40)}$=0.47, p=0.50; right, length: $F_{(1,40)}$=10.85, p=0.002; genotype: $F_{(1,40)}$=20.37, p<0.0001; length X genotype: $F_{(1,40)}$=1.13, p=0.29; Bonferroni post-test, p<0.05 or <0.001; Mean±S.E.M. basal levels shown as dotted line and grey background, respectively). (b) Locomotor activity as a function of time in bPAC$^+$ and bPAC$^-$ larvae during exposure to blue-light of either 1 or 2.8 mW*cm$^{-2}$. (c) Average locomotor activity during blue-light exposure ($t_{(79)}$=3.02, **p=0.003 for bPAC$^+_{1\ mW*cm^{-2}}$ vs bPAC$^-_{1\ mW*cm^{-2}}$; $t_{(61)}$=2.10, *p=0.04 for bPAC$^+_{2.8\ mW*cm^{-2}}$ vs bPAC$^-_{2.8\ mW*cm^{-2}}$; $t_{(70)}$=4.19, ***p<0.0001 for bPAC$^-_{1\ mw*cm^{-2}}$ vs bPAC$^-_{2.8\ mW*cm^{-2}}$; $t_{(70)}$=0.97, p=0.33 for bPAC$^+_{1\ mW*cm^{-2}}$ vs bPAC$^+_{2.8\ mw*cm^{-2}}$, t test). (d) Repeated blue-light exposures (inter trial interval: 27 min) impair stimulation-dependent cortisol increase in bPAC$^-$ but not in bPAC$^+$ larvae (Two-Way ANOVA, repeated exposure: $F_{(2,50)}$=12.44, p<0.0001; genotype: $F_{(1,50)}$=18.55, p<0.0001; repeated exposure X genotype: $F_{(2,50)}$=0.13, p=0.88; light intensity: 2.8 mW*cm$^{-2}$); note that the bPAC$^+$, but not the bPAC$^-$ larvae, responded to repeated exposures with increased cortisol (Wilcoxon signed rank test and one sample t test, respectively, *p<0.05, p<0.01 or *p<0.001). (e) Locomotor activity over repeated blue-light exposures; blue bars and black arrows indicate light exposures and times of cortisol extraction, respectively; both groups of larvae differed in their average locomotor activity (measured over a 10-min. period) tens of minutes after the light-offset (not shown) (Two-Way ANOVA, repeated exposure: $F_{(2,306)}$=3.0, p=0.0513; genotype: $F_{(1,306)}$=8.26, p=0.0043; repeated exposure X genotype: $F_{(2,306)}$=0.19, p=0.83). (f) Locomotor activity plotted against cortisol level; note that tens of minutes after the light-offset locomotion shows linear dependence of past peak cortisol level.

Figure 4:
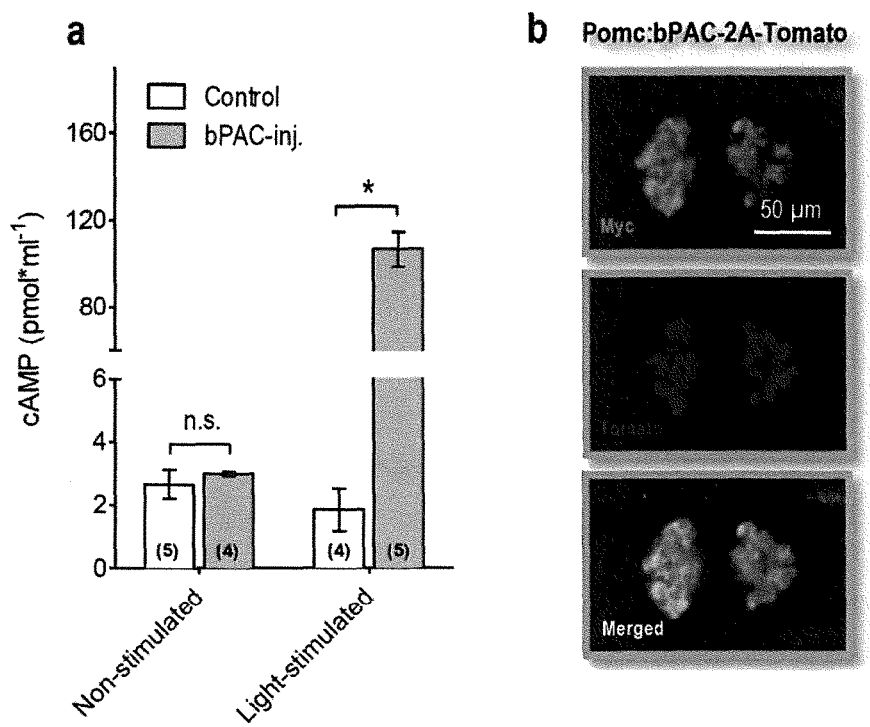

FIG. 4: Blue-light dependent rise in whole-body cAMP level and co-localization of myc-tag and tdTomato signal in bPAC-positive larvae. (a) Blue-light dependent rise in whole-body cAMP level in 1 day post fertilization (dpf) embryos after injection of bPAC mRNA into one-cell stage embryos (Mann-Whitney test, p=0.19 for non-stimulated control versus bPAC-injected; *p=0.02 for light-stimulated control versus bPAC-injected). (b) Dorsal confocal images of the pituitary of a 6 dpf bPAC-positive larva showing co-localization of myc-tag and tdTomato signal.

Figure 5:
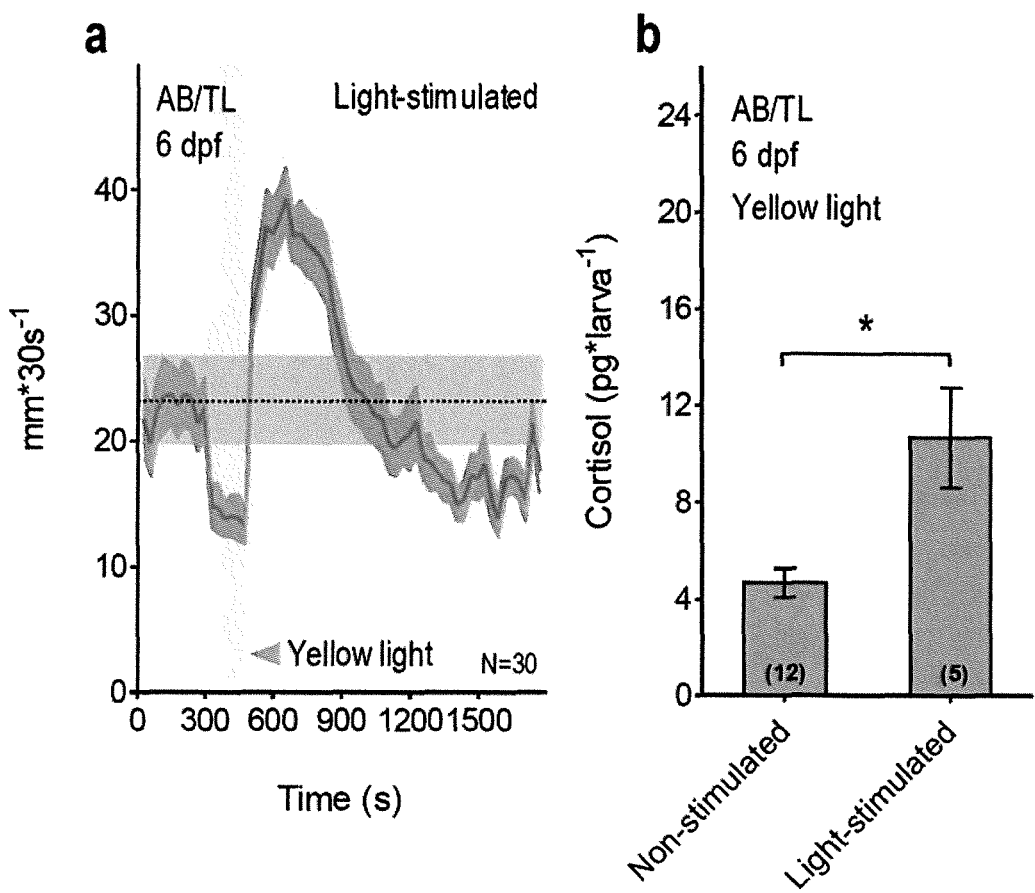

FIG. 5: Behavioral and endocrine profiles in wild-type larvae exposed to yellow-light stimulation. (a) Exposing dark-adapted wild-type larvae to yellow-light causes a fast decrease in motion followed by increased locomotion after the light-offset, similar to the motion profile caused by blue-light exposure. (b) A 180s exposure to yellow-light increases cortisol level in dark-adapted wild-type larvae (Mann-Whitney test, *p=0.03).

Figure 6:
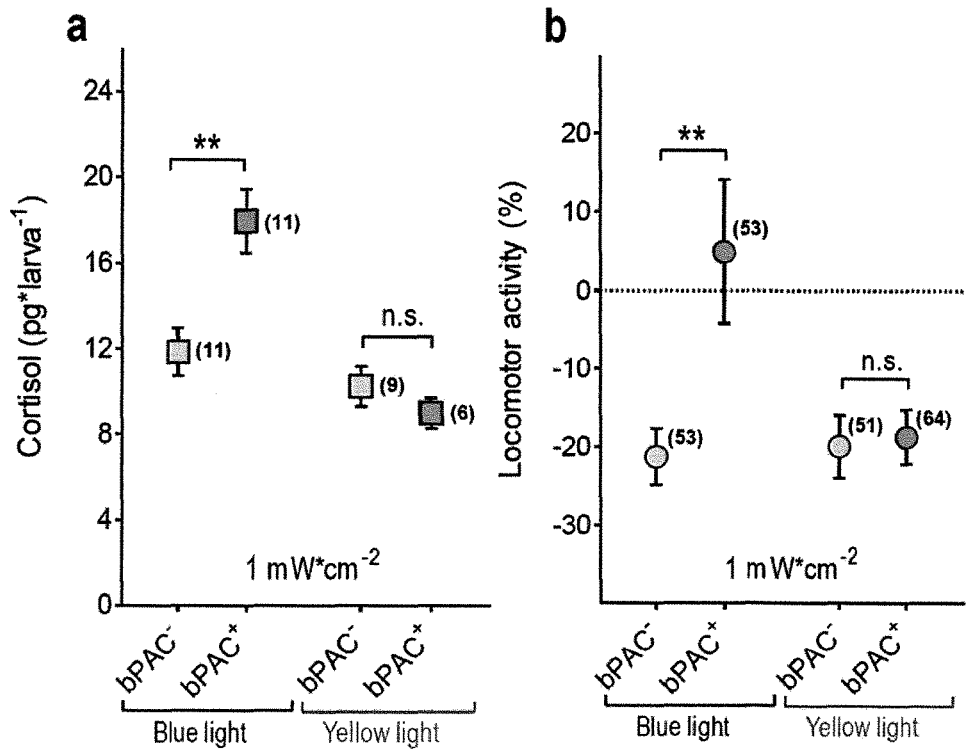

FIG. 6: Light-induced variations in glucocorticoid level and locomotor activity in in bPAC+ and bPAC− larvae exposed to either blue- or yellow-light. (a) Cortisol level in bPAC+ and bPAC− larvae 2 min. after a 180s exposure to either blue or yellow-light of equal intensity (Mann-Whitney test, **p=0.002 for blue-light-stimulated bPAC− versus bPAC+; p=0.46 for yellow-light-stimulated bPAC− versus bPAC+). (b) Average locomotor activity in bPAC+ and bPAC− larvae (measured over a 10 min. period; in %, relative to pre-stimulation baseline) after the offset of either blue- or yellow-light of equal intensity (Mann-Whitney test, p=0.04 and p=0.70 for bPAC-positive versus negative larvae exposed to blue and yellow-light, respectively).

Figure 7:
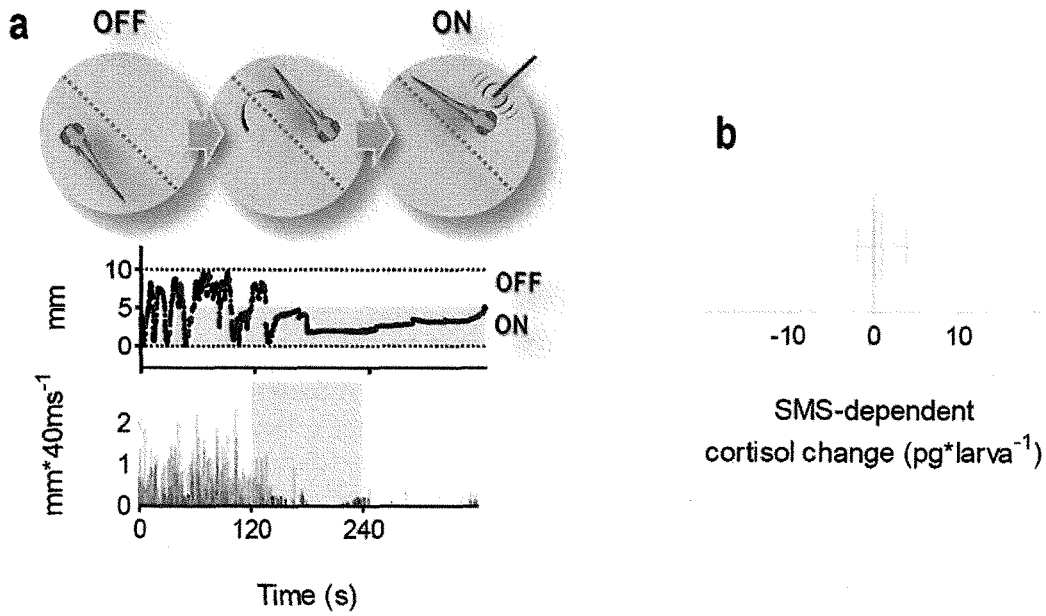

FIG. 7: The response of larval zebrafish to subtle mechanosensory stimulation (SMS) involves active components and does not alter glucocorticoid level. (a) SMS occurring only when the larva being recorded swims within the half of the chamber containing the stimulation source; exemplary tracks depicting the distance to the stimulation source (top) and swimming velocity (bottom) as a function of time; pink backgrounds indicate repeated SMS (applied at 1 Hz for 120s). (b) Depicted in the cortisol level of 6 dpf larvae exposed to SMS relative to that of none-exposed larvae.

Figure 8:
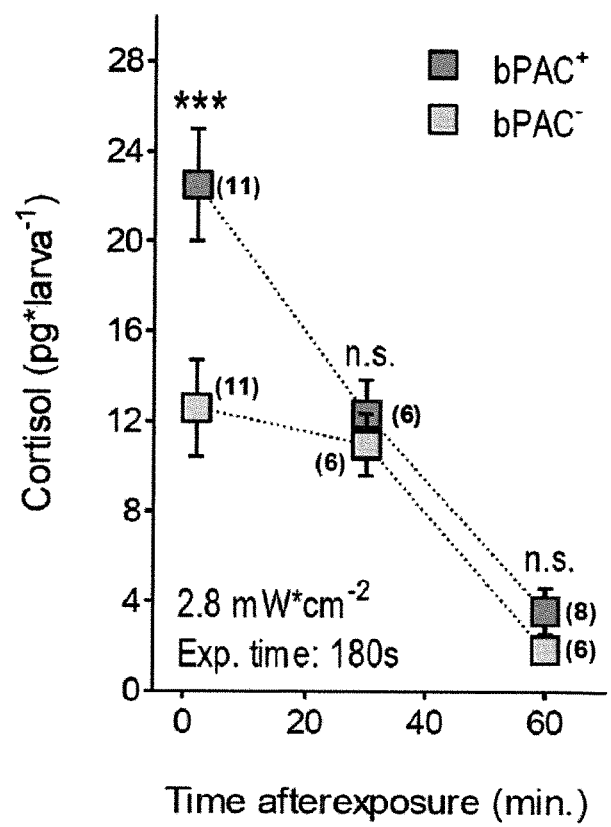

FIG. 8: Cortisol level as a function of time after blue-light stimulation. Cortisol levels in bPAC+ and bPAC− larvae measured at different times after a 180s exposure to blue-light of 2.8 mW*cm−2 (Two-Way ANOVA, time: F(2,42)=28.43, ***p<0.0001; genotype: F(1,42)=23.09, p=0.0153; time X genotype: F(2,42)=3.18, p=0.06; Bonferroni post-test for pair comparisons, p<0.01).

Figure 9:
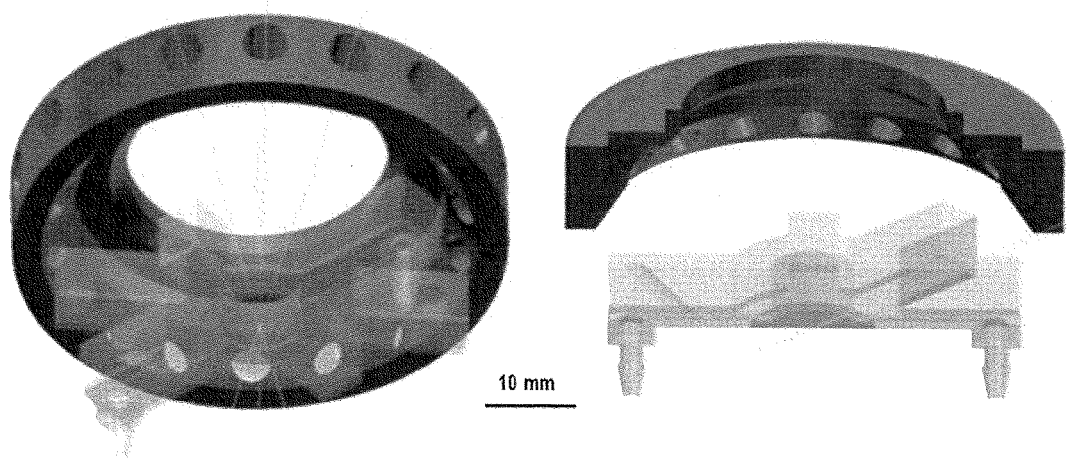

FIG. 9: LED-array and swimming chamber. Perspective views of the array of LEDs pointing toward the center of the custom-made swimming chamber.

Figure 10:
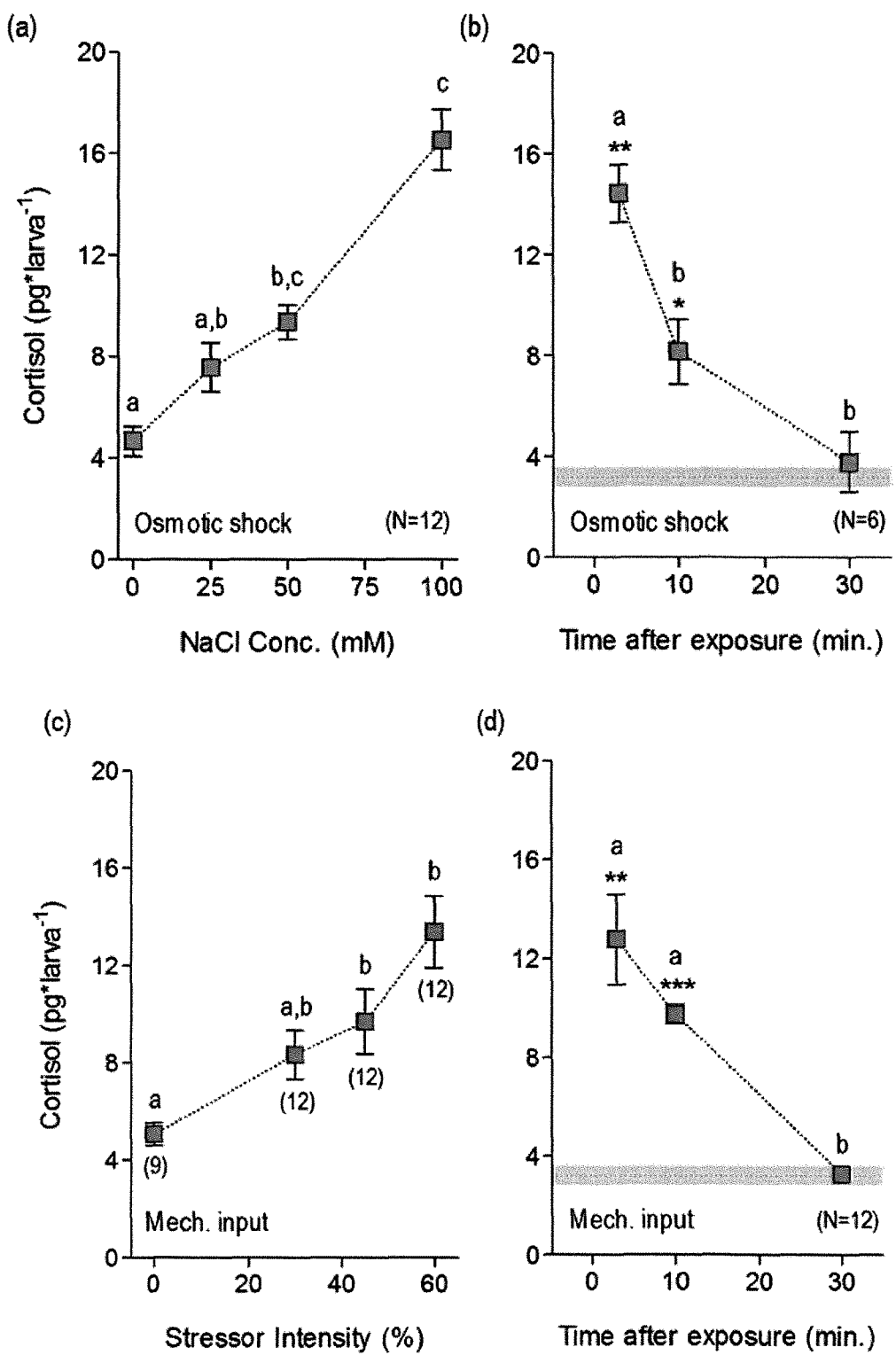

FIG. 10: HPI-axis activity as a function of stressor intensity and time after exposure. (a) A 10 min exposure to different concentrations of NaCl (osmotic shock) led to similar results (Data from 6 dpf AB/TL larvae; sample size in parenthesis). (b) Increased cortisol level decreased shortly after stressor exposure, reaching basal levels 30 min after exposure to 100 mM NaCl (Data from 6 dpf AB/TL larvae; sample size in parenthesis). (c-d) Parallel results were obtained using mechanosensory input as a stressor. Cortisol level increased together with the intensity (Data from 5 dpf AB/TL larvae; sample size in parenthesis) and cortisol levels decreased shortly after exposure to 60% stressor intensity (Data from 6 dpf AB/TL larvae; sample size in parenthesis). Asterisks designate statistical differences relative to average basal cortisol level (±S.E.M., dashed line and above and below gray zones, respectively) (*$p<0.05$, $p<0.01$, *$p<0.001$, One sample t-tests and Wilcoxon Signed Rank tests). Different letters specify statistical differences as determined by one-way ANOVAs, followed by post-hoc comparisons.

Figure 11:
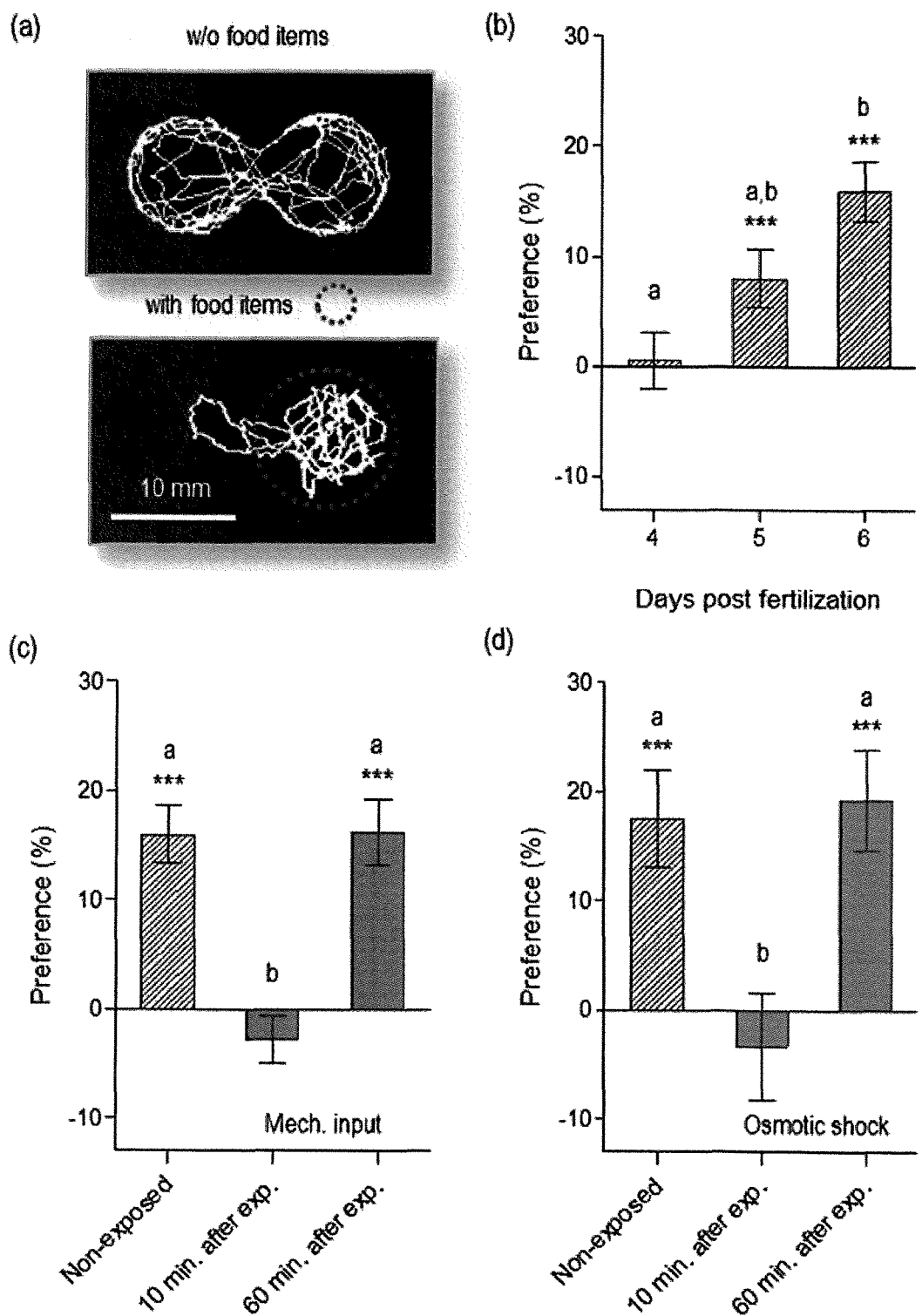

FIG. 11: Stressor exposure reversibly impairs feeding motivation. (a) Exemplary traces of 6 dpf AB/TL larvae during a 10 min recording period showed a side preference that could only be detected in the presence of food items (red dashed circle). (b) Preference was absent at 4 dpf and increased significantly with age ($N_{4\ dpf}=23$; $N_{5\ dpf}=20$; $N_{6\ dpf}=19$). (c) Exposure to mechanosensory input abolished side preference in 6 dpf larvae 10 min after exposure, while it was recovered 60 min after exposure (N=23). (d) Osmotic shock led to the same results in 6 dpf AB/TL; diminished side preference 10 min after exposure (N=6) and recovered side preference 60 min after exposure (N=6) indistinguishable from non-exposed larvae (N=11). Asterisks signal differences from zero (no preference) (*$p<0.05$, $p<0.01$, *$p<0.001$, Wilcoxon Signed Rank Tests). Different letters specify within group differences as determined by one-way ANOVAs, followed by post-hoc comparisons.

The examples illustrate the invention:

EXAMPLE 1

Methods

Generation of Transgenic Zebrafish cDNA encoding Photoactivated adenylyl cyclase from beggiatoa (bPAC; (Stierl et al., 2011)) was PCR-amplified with a mutated stop-codon and cloned into a vector containing a viral 2A sequence (Tang et al., 2009), as well as tdTomato flanked by I-SceI and Tol2 transposon recognition sites in pBR322 backbone. This construct was combined with a Pomc promoter which was PCR-amplified from a Pomc-GFP construct (Liu et al., 2003). The Pomc:bPAC-2A-tdTomato plasmid was diluted in water and incubated with 100 ng Tol2 transposase RNA for 10 min in order to obtain a higher efficiency of transgenesis (Kawakami, 2004). Plasmid and RNA mixture was injected into one-cell-stage wild-type embryos (cross of AB and TL strains) in the presence of 0.05% phenol red. One founder was selected with specific tdTomato expression in the pituitary and no ectopic expression for further propagation.

Zebrafish Husbandry

Zebrafish (*Danio rerio*) breeding and maintenance was performed under standard conditions (Westerfield, 2000). Embryos were collected in the morning and raised at 28.5° C. on a 12:12 hour light:dark (LD) cycle in E2 medium at a density of 6 eggs ml$^{-1}$. Rx3 mutants were intercrossed and homozygous mutants selected by morphological appearance (stronger pigmentation, lack of eyes). PAC transgenic fish were outcrossed with wildtype (AB/TL) and selected for fluorescent tdTomato expression in the pituitary between 4 and 5 dpf using a fluorescent dissecting scope. To avoid unspecific activation of PAC prior to experiments, transgenic embryos were raised in custom-made reflective containers (FIG. 4c) covered with 550 nm long pass filters (Thorlabs). Groups that were compared in a behavioral assay were always raised under the same conditions unless otherwise specified.

Behavioral Testing

Behavioral tests were carried out using wild-type, bPAC-positive and negative 6 dpf larvae. Experiments were conducted inside a custom-made light-proof enclosure placed on a vibration-free platform (Newport, Irvine, Calif., USA), under infrared (IR) light delivered via an array of IR-LEDs. The behavior setup was assembled within the enclosure using custom-made mechanic components. To image the movements of individually swimming larvae at 25 frames s$^{-1}$, an infrared-sensitive camera was used (ICD-49E B/W, Ikegami Tsushinki Co., Ltd. Japan) with its lens (TV Lens, Computar VARI FOCAL H3Z4512 CS-IR, CBC (America), NY, USA) surrounded by a custom-made LED ring light positioned above a custom-made swimming chamber (FIG. 9) or a tissue culture plate (Greiner-Bio One, Germany), depending on the experiment (see below). The array of IR-LEDs illuminated the chamber or the tissue plate from below. EthoVision XT software (Noldus Information Technology, The Netherlands) was used to track the larvae's swimming paths. The swimming chamber made of glass and Plexiglas had an inner diameter of 10 mm and four openings, and held a volume of 400 µL. Two of such openings (height: 400 µm, width: 2.5 mm) were the inlet and outlet channels, as experiments were conducted with E2 medium (Westerfield (2000)) circulating within the chamber (see below). The remaining two openings were cylindrical channels of 400 µm in diameter symmetrically positioned at each side of the chamber, with their longest axis oriented at an angle of 30° relative to horizontal; both these channels opened at the transparent glass bottom of the chamber. One of these two cylindrical channels held a reference thermocouple (npi electronics GmbH, Tamm, Germany) to constantly monitor the temperature within the chamber. The second channel held a silica capillary used to deliver subtle, highly controlled mechanosensory stimuli (see below). Using a peristaltic pump (IPC Ismatec (IDEX Health & Sciences GmbH, Glattbrugg, Germany), a 200 µL*min.$^{-1}$ flow rate of E2 medium (Westerfield (2000)) was set within the chamber. This flow rate had no detectable influence on the larvae's nominal level of locomotion and allowed to control the average temperature within the chamber (kept at 28.0±0.5° C.) using a temperature control system (PTC 20, npi electronics GmbH, Tamm, Germany; Exos-2 V2 liquid cooling system, Koolance, Auburn, USA). For long-term recordings, the tissue culture plate were used to simultaneously image the movements of 30 larvae at 26-28° C., each placed in 40 µL of E2 medium, whereas the remaining experiments were made using the above described swimming chamber. All the experiments involving transgenic larvae were blind and the different experimental groups were intermixed throughout the day. Tests were performed during hours matching the larvae's daytime. In all experiments, the larvae were given 15 minutes to adjust to the test conditions prior to recording.

Reaction to temperature change. The temperature control system allowed to quickly and precisely modify the temperature of the flowing medium so as to generate asymmetric temperature variations within the small chamber. By rapidly increasing the temperature of the inflowing medium in a highly controlled, reproducible manner (FIG. 2a), the aim was to increase not only the average temperature within the chamber, but also the temperature difference between the zones 1 (high temp.) and 2 (low temp.), near the inlet and outlet, respectively (FIG. 2b,c), so as to maximize the probability of detecting reactions to temperature change giving the small dimensions of the chamber. The temperature measurements in zones 1 and 2 (FIG. 2b) were carried out in the absence of larvae. After initial adjustment to the test conditions (see above), each session involved a 240s measurement of baseline locomotion under constant temperature, followed by a 300s measurement of motion level under the temperature change regime. First the increase in velocity (in percentage) was calculated that occurred during the 30s time period when the temperature difference between the zones (i.e. 1 and 2) increased at a maximum rate, as $((Vel_{90s}-Vel_{60s}/Vel_{60s})*100)$. To estimate stimulus responsiveness, the relative difference in velocity in zones 1 and 2 was calculated, as $((Vel_{zone1}-Vel_{zone2}/Vel_{zone2})*100)$ measured at 0 and 180s after the onset of temperature increase.

Feeding

Freely behaving larvae were placed individually in small custom-made swimming chambers consisting of two interconnected compartments (see FIG. 10a). Next, their motion pattern was recorded under white light illumination during a 20 minute period, first in the absence of food items (initial 10 minutes) and then after having added 40 pl paramecia to one of the chamber's compartments (final 10 minutes). Measures of locomotion level (distance moved per unit time) and space use (proportion of time spend in either compartment of the chamber) were then calculated and compared across groups.

Subtle mechanosensory stimulation (SMS). Experiments were conducted with single larvae swimming within the custom-made chamber. A silica capillary (diameter: 350 µm) was introduced 1 mm into the swimming chamber through one of its two cylindrical channels (see above). The capillary was fixed to a piezo actuator (PL 140.10 (Physik-Instrumente, Karlsruhe, Germany) in turn connected to a pulse generator (Universal Taktgenerator, EL V GmbH, Leer, Germany). This allowed to move the capillary laterally, controlling the duration and strength of such movements by modifying the voltage applied to the piezo actuator; this voltage is referred to as the strength of SMS of a given duration or stimulus intensity. In the experiments reported here, a single SMS unit consisted of ten lateral movements of the capillary, each lasting 1 ms and delivered with an intertrial interval (i.t.i.) of 1 ms. When presented consecutively, SMS units were delivered at a frequency of 1 Hz. Two types of SMS protocols were used. In the first one, SMS occurred only when the larva being recorded swam within the half of the chamber containing the capillary (FIG. 7a). In the second protocol, baseline motion was first measured during 120s and then SMS applied as described above for a 120s period. To quantify the strength of the larvae's response to SMS, for each larva the distance swam every 40 ms 'before' and 'during' the initial 120s SMS period was first plotted, and then the corresponding 'distance swam vs time' integrals was calculated. Next, to estimate the magnitude of the drop in motion caused by SMS, the areas under the curve from both such integrals (i.e. before and during) as well as the net area difference was calculated. The inverse of this value was considered to be a response strength derivative and is referred to as the 'response strength'. Finally, the light-induced response enhancement shown in FIG. 2j was defined as $(('response strength'_{light-stimulated}-\text{response strength}_{none-stimulated})/\text{response strength}_{none-stimulated})*100)$.

Light stimulation. A custom-made LED ring light surrounding the camera lens was placed above the recording chamber (see above). The incident angle of the LEDs permitted homogeneous illumination of either the swimming chamber (FIG. 4h) or the tissue plate. To control the LEDs, custom-made drivers, pulse generators and a TTL control box (USB-IO box (Noldus, Wageningen, The Netherlands) were used. In the experiments reported here, the larvae were exposed to either blue- or yellow-light of varying intensity for 18s or 180s. Light power was measured using a hand-held light power meter (Newport, USA). Each light pulse consisted of 100 ms flashes delivered at a frequency of 5 Hz.

Osmotic Shock

Larvae were exposed to different concentrations of NaCl solutions for 10 min in darkness at 28° C. For subsequent recordings larvae were washed in E2 medium and transferred to the recording chamber. Control larvae were exposed to E2 in the same manner to rule out any effect of handling. Recordings were started within a time window of 4-5 min after the end of stressor exposure. In experiments addressing behavioral correlates of osmotic stress, larvae were exposed to 50 mM NaCl.

Strong Mechanosensory Input

In order to apply strong mechanosensory stimulation to the larvae, a multilayer bender actuator (PICMA® PL140.10) with an operating voltage of 0-60V, a nominal displacement of (±1000 µm), and an unloaded resonant frequency of 160 Hz was used. The bender was coupled to a pulse generator, a dual-piezo-amplifier with an adjustable gain and a 10-turn precision potentiometer which boosts an input signal of 10V to an output signal of 0-60V, and a TTL control system allowing computer control. A silica capillary tube (Polymicro Technologies, AZ) was glued to the bender and placed, partially submerged (~2mm), at the center of a 35 mm petri dish half filled with E2 medium. Six units of strong mechanosensory stimulation were applied with different intensities and frequencies (3V 2 Hz, 4.5V 6 Hz, and 6V 10 Hz). Every unit started immediately after the previous and contained 99 pulses each 40 ms in duration with varying i.t.i. Stimulation was performed at RT under normal daylight illumination. In each of the experiments addressing behavioral correlates of mechanosensory stress, an intensity and frequency of 6 V and 10 Hz, respectively, were used. After the exposure, larvae were transferred to the recording chamber and remained unperturbed for 10 minutes in order to adjust to the new environment before the beginning of the recording session.

Cortisol Measure

Groups of 30 larvae (6 dpf) were stimulated, immobilized in ice water, immediately frozen in ethanol/dry and stored at −20° C. Cortisol was extracted by homogenizing the samples in 150 µL ddH2O. Afterwards, 1 mL ethyl acetate was added to the homogenized samples, vortexed for 30 s, and centrifuged for 5 min at 5000×g and 4° C. In order to separate the cortisol containing solvent from the aqueous phase, the samples were put in −50° C. ethanol/dry ice, allowing only the aqueous phase to freeze and decanting the cortisol containing solvent into a new tube. Ethyl acetate was evaporated 30 min at 30° C. in a speed-vac concentrator and cortisol re-dissolved in 60 µL sample-buffer. An ELISA plate (Immulon 2HB) was coated with cortisol mouse antibody (EastCoast Bio, Inc.) (4 µg/mL in 1×PBS) overnight at 4° C. in darkness. Next, after three washing steps using 250 µL washing buffer each, 200 µL blocking buffer were added and the preparation incubated for 30 min at RT on an orbital shaker at 40 rpm to reduce unspecific binding, followed by washing. 50 μL of each sample along with a standard (Hydrocortisone, Sigma-Aldrich) were pipetted into the plate. 50 μL Cortisol-HRP (EastCoast Bio, Inc.) in a final dilution of 1:400 in 1×PBS were added to each well and the preparation incubated for 2 h at RT. After three washing steps, 100 μL staining-solution was added to each well and incubated for 30 min at RT. The reaction was stopped by adding 100 μL stop-solution (1 M sulfuric acid) and the plate briefly shaken before measuring absorption at 450 nm with an ELISA-reader (Thermo Scientific Multiskan Ascent). The measured optical density of the standard and its corresponding cortisol concentration was plotted in a logit-log plot, and the cortisol concentrations of the samples calculated from the ensuing linear regression line. The results were corrected for the dilution factor, extraction efficiency and recovery function. Unless otherwise stated, cortisol samples were taken two minutes after the offset of either light or SMS (see below).

cAMP Measurement 50 pg capped bPAC RNA was prepared using mMessage mMachine T7 Ultra Kit (Ambion) and injected into one-cell-stage AB/TL embryos. Embryos were maintained in the reflective, light-filtering containers and subjected to blue light at 1 day post fertilization (dpf) using the light protocol described below (light intensity: 2.8 mW cm$^{-2}$). Groups of 27 embryos were collected immediately after the light-offset and instantly homogenized in 210 μl 0.1 M HCl on ice. After centrifuging at 12000×g for 30 minutes at 4° C., the supernatant was extracted and stored in −20° C. cAMP level was measured following the acetylation protocol from a cAMP ELISA kit (ADI-900-066, Enzo Life Sciences). 100 μl of the sample were used for the assay and blue light stimulated bPAC injected samples were diluted 15 times to allow measurement within the standard range. Results were calculated by interpolating the % of the samples bound to the standard curve.

Immunohistochemistry

Six dpf larvae were fixed in 4% paraformaldehyde (PFA) in phosphate-buffered saline (PBS) overnight at 4° C. Immunohistochemistry was performed as previously described (Ryu, S. et al. Curr Biol 17, 873-880, (2007)) using polyclonal antibody against human ACTH (National Hormone and Peptide Program, National Institute of Diabetes and Digestive and Kidney Diseases; 1:500) or rabbit polyclonal antibody against Myc-Tag (Cell Signaling Technology; 1:500) as primary antibodies and Alexa488 anti-rabbit (Invitrogen; 1:1000) as a secondary antibody, overnight at 4° C. on a shaker (30-40 rpm) protected from light. Larvae were imaged in 80% glycerol buffer using Leica SP5 CLSM with a Nikon 20×glycerol objective. Stacks were evaluated using Amira 5.4 to create maximum intensity projections and to evaluate voxel correlations across channels.

Statistical Analysis.

All data are shown as mean and standard error of the mean (S.E.M.). For the sake of comparison, locomotor activity is expressed in percentage relative to pre-stimulation baseline level, unless otherwise stated, since baseline levels did not differ between the bPAC-positive and negative larvae (Mann-Whitney test, p=0.11). Student's t tests (two-tailed) were used for two-group comparisons, or Mann-Whitney U-tests were used if the data did not fulfill the assumptions of the t test. Linear regressions and ANOVAs were used for multiple group comparisons, followed by Bonferroni's post-hoc tests, or their non-parametric equivalent. The data were analyzed using MS-Excel (Microsoft, Redmond, Wash., USA), Matlab 2009b (MathWorks, Natick, Mass., USA), Prism 5, (Graphpad Software Inc., San Diego, Calif., USA), Sigma Plot (Systat Software Inc., San Jose, Calif., USA) and Virtual Dub (Freeware).

EXAMPLE 2

Optogenetic Induction of Endogenous Hypercortisolaemia in Larval Zebrafish

Glucocorticoids (GCs) are the end product of the evolutionary conserved mediator of the stress response, the hypothalamo-pituitary-adrenocortical (HPA) axis. To study the contribution of GCs to stress-dependent behavioral alteration, it is necessary to alter the level of endogenous GCs without varying upstream neuroendocrine pathways simultaneously. Currently no effective method exists to specifically manipulate GC-level, since the injection of exogenous GCs in itself is stressful and does not provide the resolution required for dissecting GC effects across time domains.

The stress response involves a repertoire of physiological and behavioral processes that counteracts a threat to homeostasis. It relies on the hypothalamic-pituitary-adrenocortical (HPA) axis, whose activation leads to coupled release of corticotropin-releasing-hormone (CRH), adrenocorticotropin (ACTH) and glucocorticoids (GCs) (Charmandari et al. (2005)). While the main function of ACTH is to stimulate GC release, both CRH and GC have receptors with wide distribution and have been implicated in a variety of stress correlates (Lowry and Moore (2006); McEwen and Sapolsky (1995); Sandi and Pinelo-Nava (2007)). The mechanistic dissection of GC-function is challenging because GCs have pleiotropic functions acting in different temporal domains, ranging from milliseconds to days (Griffiths et al. (2012); Charmandari et al. (2005)). To understand specific GC-functions, it is necessary to alter GC-level with similar levels of hypothalamus activation, yet currently no effective method exists to specifically manipulate endogenous GC-level.

Thus, an optogenetic approach was used to non-invasively and selectively change the level of endogenous cortisol, the main GC in teleost, in larval zebrafish, whose hypothalamic-pituitary-interrenal (HPI) axis matures early in development and is homologous to the HPA-axis in mammals (Lowry and Moore (2006); McEwen and Sapolsky (1995)). Further, the interaction of GC and serotonin signaling is conserved in zebrafish (Sandi and Pinelo-Nava (2007); Sapolsky et al. (2000)). The gain of the HPI-axis was optogenetically modified to achieve different GC-levels in animals exposed to otherwise identical stressful events, and correlated variations in glucocorticoid level, locomotor activity and stimulus responsiveness were examined.

Larval zebrafish are highly sensitive to photic stimuli (Burgess and Granato (2007)), and react to sharp transitions from darkness to light by a suppression of locomotion followed by increased locomotion after the light-offset (MacPhail et al. (2009)). It was observed that larvae react similarly to blue-light illumination (FIG. 1a,b) which leads to increased cortisol levels shortly after light exposure (FIG. 1c). Therefore, to differentially increase cortisol levels without affecting CRH, the expression of beggiatoa photoactivable adenylyl cyclase (bPAC) (Stierl et al. (2011); Ryu et al. (2010)) was targeted to pituitary corticotrophs, which produce ACTH (FIG. 1d, e).

It was hypothesized that increase in cAMP upon activation of CRH receptor 1 (CRHR1) in these cells can be mimicked using blue-light stimulation of bPAC, thereby enhancing ACTH and cortisol release.

First, a blue-light dependent rise in whole-body cAMP level using bPAC mRNA in zebrafish was demonstrated (FIG. 4a).

Next, using a fragment of proopiomelanocortin (POMC) promoter (Liu et al. (2003)), bPAC coupled to tdTomato was targeted specifically to the pituitary corticotrophs, restricted to two cell clusters in the whole larvae (FIG. 1f). Fluorescent tdTomato signal co-localized with bPAC, as detected by fused myc-tag (FIG. 4b), and also with ACTH (FIG. 1f)Both bPAC-positive and negative larvae responded to blue-light with increased cortisol, consistent with our observation that light itself acts as a stressor. However, the positive larvae showed higher cortisol levels than the negative ones (FIG. 1g). Further, although exposure to both blue- and yellow-light led to similar behavioral and endocrine profiles in wild-type larvae (FIG. 1a-c and FIG. 5a,b), yellow-light failed to enhance cortisol change in the bPAC-positive larvae (FIG. 6a), in line with the fact that bPAC is specifically activated by blue-light due to its BLUF (blue-light receptor using FAD) type light sensor domain (Stierl et al. (2011)). Since GCs mobilize energy and enhance locomotion (Sandi et al. (1996)), it was next analyzed whether such a differential increase in cortisol had detectable motion correlates. It was observed that the bPAC-positive larvae showed enhanced locomotion after the offset of blue- (FIG. 1h) but not of yellow-light (FIG. 6b). Taken together, these results show that this approach can generate different levels of endogenous cortisol and post-stressor locomotor activity via identical stimulation protocols, thereby preserving analogous levels of hypothalamus activation.

Stress influences behavior in multiple ways, ranging from immediate changes in locomotion to alterations in arousal, feeding, learning and memory. In particular, it can modify an organism's control properties so as to increase its responsiveness to environmental stimuli (Pfaff et al. (2008)). Therefore, in order to validate the present approach, it was asked whether optogenetically enhanced cortisol levels can modify the responsiveness of larval zebrafish to external stimulation. To test this prediction, the reaction of individual larvae to highly controlled temperature variations was measured (FIG. 2a-c); temperature was used as a source of external input because larval zebrafish are strictly exothermic and their locomotor activity increases with temperature change (Prober et al. (2008)). Shortly after blue-light stimulation, the positive, but not the negative larvae, reacted rapidly to contact with rising temperatures by increasing their turns (not shown) and swimming velocity (FIG. 2d). This led to conspicuous group differences in stimulus responsiveness (FIG. 2e). To rule out stimulus specificity, a hitherto unreported response of larval zebrafish to subtle mechanosensory stimulation (SMS) was characterized next. Next, light-induced response enhancements were measured. It was observed that larval zebrafish respond to SMS by approaching the source of stimulation and, subsequently, by progressively reducing their rate of discontinuous motion (FIG. 2f-h), a response that is graded (FIG. 2i), active and non-stressful (FIG. 7a,b). Blue-light exposure of low intensity enhanced SMS responsiveness specifically in the positive larvae, whereas a higher light-intensity greatly enhanced responsiveness in both groups (FIG. 2j), indicating that this response is highly sensitive to stress. Altogether, these results demonstrate that optogenetically enhanced cortisol levels strengthen stimulus responsiveness in larval zebrafish, presumably by shifting response thresholds (FIG. 2k). GCs are known to mediate rapid stress reactions (Moore and Orchinik (1994)), but their effects are difficult to dissect because injections of exogenous GCs are stressful and do not provide sufficient resolution. To examine whether rapid GC effects can be detected on locomotion, it was first tested whether brief light stimulations were sufficient to increase cortisol. A brief exposure to blue-light of low intensity lasting only several seconds was sufficient to increase cortisol in the positive but not in the negative larvae, and the longer the stimulation the higher the ensuing cortisol level. By contrast, a higher light intensity increased cortisol in both groups, but the bPAC-positive larvae showed higher levels than the negative ones; as before, the longer the stimulation the higher the cortisol level (FIG. 3a). To the inventors surprise, the bPAC-positive and negative larvae moved differently already during blue-light exposure, with the positive larvae displaying comparatively lower and higher motion levels with increasing light intensity (FIG. 3b,c). These results show that rising cortisol levels have fast, detectable changes in mobility, and that these changes can be of a different sign, depending on the rate of cortisol change.

Stress raises GC-levels but negative feedbacks by GCs onto the hypothalamus and pituitary terminate the stress response (Dallman et al. (1994); Dallman, and Yates (1969)). Impairment of such feedbacks caused by excess of ACTH and GCs, as in Cushing's syndrome, can lead to a state of hypercortisolaemia, a major health risk in humans (Wolkowitz et al. (2009)). Cushing's disease-like hypercortisolism can be mimicked in zebrafish by targeting corticotroph tumor growth and hormone secretion (Liu et al. (2011)), yet this approach does not allow temporal control of hypercortisolaemia. It was therefore asked whether the modification of the gain of the HPI-axis at the level of the pituitary can lead to a form of hypercortisolaemia. Twenty minutes after a single blue-light exposure both bPAC-positive and negative larvae had significantly reduced cortisol levels, which reached basal levels forty minutes later (FIG. 8). In stark contrast, the positive but not the negative larvae responded to repeated light exposures with increased cortisol (FIG. 3d). It was next examined how this form of hypercortisolaemia related to the larvae's locomotor activity, and it was observed that bPAC-positive larvae showed enhanced locomotion tens of minutes after the light-offset (FIG. 3e). The resulting motion values, plotted against the cortisol levels from the several exposures, could be approximated by a linear regression (FIG. 3f, R-squared=0.97). These data demonstrate that, in animals repeatedly exposed blue-light, increasing the gain of the HPI-axis at the level of the pituitary leads to hypercortisolaemia and deviations from nominal locomotion.

The previously existing inability to alter endogenous GC-levels with high temporal resolution has made it difficult to pin-down specific roles of GCs in regulating stress reactions. In this example it is shown that the gain of their HPI-axis can be optogenetically modified in larval zebrafish, altering endocrine and behavioral stress reactions. Zebrafish entertains a repertoire of genetic tools and the larvae's translucent body as well as its oviparous development makes it ideal for non-invasive brain imaging and optogenetic probing of neuronal circuitry. This study presents a promising novel approach for the analysis of GC-function, including feedbacks within the stress axis and developmental programming.

EXAMPLE 3

Direct Responses to Stressors in Larval Zebrafish

Empirically, stressors are stimuli leading to ACTH release by pituitary cells, subsequently triggering the release of glucocorticoids by cells in the adrenal cortex. In adult teleosts, variation of temperature, salinity, turbidity, heavy metals, and pH increases glucocorticoid levels (Wendelaar Bonga, 1997). Previous (unpublished) data showed that various stressors increase whole-body cortisol levels in larval zebrafish, as well. Mechanosensory perturbations of the surrounding medium, osmotic shock, temperature change, ammonia, copper sulfate (CuSO4) and ethanol, all led to increased cortisol levels, relative to controls. As is shown in FIG. 10, a stressor intensity-dependent cortisol increase is observed in larval zebrafish exposed to osmotic shock, (FIG. 10a), and a post-peak cortisol decline can be seen after stressor exposure (FIG. 10b). A second stressor, namely mechanosensory input, was further employed to precisely control stressor intensity. Here, a graded perturbation of the medium using a piezo element to produce precise vibration was used, which is different from swirling as previously employed. In line with the results on osmotic shock, cortisol showed a positive correlation with stressor intensity of mechanosensory input (FIG. 10c; $F(3,44)=7.64$, $p<0.001$). The decay of cortisol levels with time after exposure (FIG. 10d; $F(2,14)=20.19$, $p<0.001$) could also be confirmed. Post peak cortisol levels in both cases, osmotic shock and mechanosensory input, could not be distinguished from initial basal levels (dashed lines with gray zones) 30 min after stressor exposure.

EXAMPLE 4

Stressor Exposure Reversibly Reduces the Larvae'S Motivation to Feed

A well-known behavioral stress response in vertebrates is a reduction in food intake (Carr, 2002). In zebrafish development, the yolk sack begins to deplete around 3 dpf (Kimmel et al., 1995) and larvae need to start actively feeding. Thus, the question arose whether this phenomenon can also be found in developing zebrafish. In order to address this question, larval zebrafish were exposed to stressors and subsequently tested for their feeding motivation.

First, a measure of feeding behavior needed to be developed. This was achieved via indirectly assessing feeding motivation as differential space use in a two-compartment swimming chamber where food was offered in one compartment only (FIG. 10a). At 4 dpf no preference could be detected, while at 5 and 6 dpf side bias towards food items was significant. Overall feeding motivation increased significantly with age (FIG. 10b; ANOVA $F(2,61)=8.50$, $p<0.001$).

To test the effect of stressor exposure, 6 dpf larvae were treated with mechanosensory input, which was previously found to elevate cortisol levels (see Example 3). The treatment abolished side preference entirely, indicating a reduction in feeding motivation (FIG. 11c). Such effect was reversible, as larvae showed feeding motivation indistinguishable from untreated controls when given 60 min to recover after stressor exposure. Overall the effect of treatment was highly significant (ANOVA $F(2,68)=16.56$, $p<0.001$). To rule out the possibility of a stressor-specific phenomenon, exposure to osmotic shock was tested as well. The results confirmed the previous ones, showing an initially reduced feeding motivation that was regained 60 min after stressor exposure (FIG. 4d; ANOVA $F(2,22)=5.79$, $p=0.010$).

REFERENCES

Agulleiro M J, Roy S, Sanchez E, Puchol S, Gallo-Payet N, Cerda-Reverter J M (2010) Role of melanocortin receptor accessory proteins in the function of zebrafish melanocortin receptor type 2. Molecular and Cellular Endocrinology 320 (2010) 145-152

Alderman S L, Bernier N J (2009) Ontogeny of the corticotropin-releasing factor system in zebrafish. General and comparative endocrinology 164:61-69.

Alsop D, Vijayan M (2009) The zebrafish stress axis: molecular fallout from the teleost-specific genome duplication event. General and comparative endocrinology 161:62-66.

Alsop D, Vijayan M M (2008) Development of the corticosteroid stress axis and receptor expression in zebrafish. Am J Physiol Regul Integr Comp Physiol 294:R711-719.

Anikeeva P, Andalman A S, Witten I, Warden M, Goshen I, Grosenick L, Gunaydin L A, Frank L M, Deisseroth K. Optetrode: a multichannel readout for optogenetic control in freely moving mice. Nat Neurosci. 2011 Dec. 4; 15(1):163-70. doi: 10.1038/nn.2992.

Arzt, E. and Holsboer, F. (2006) CRF signaling: molecular specificity for drug targeting in the CNS. Trend Pharmacol. Sci. 27: 531-538

Bale T L, Vale W W (2003) Increased depression-like behaviors in corticotropin-releasing factor receptor-2-deficient mice: sexually dichotomous responses. J Neurosci, 23, 5295-5301.

Belzung C., Griebel G., Measuring normal and pathological anxiety-like behaviour in mice: a review Behav Brain Res, 125 (2001), pp. 141-149

Burgess H A, Granato M (2007) Modulation of locomotor activity in larval zebrafish during light adaptation. The Journal of experimental biology 210:2526-2539

Carr J A (2002) Stress, neuropeptides, and feeding behavior: a comparative perspective. Integrative and comparative biology 42:582-590

Charmandari, E., Tsigos, C., and Chrousos, G. (2005) Endocrinology of the stress response. Annu Rev Physiol. 67:259-84.

Chung S, Son G H, Kim K (2011) Circadian rhythm of adrenal glucocorticoid: its regulation and clinical implications. Biochimica et biophysica acta 1812:581-591

Chrousos G P, Gold P W (1992) The concepts of stress and stress system disorders. Overview of physical and behavioral homeostasis. JAMA: the journal of the American Medical Association 267:1244-1252.

Dallman M F, Akana S F, Levin N, Walker C D, Bradbury M J, Suemaru S, Scribner K S (1994) Corticosteroids and the Control of Function in the Hypothalamo-Pituitary-Adrenal (HPA) Axisa. Annals of the New York Academy of Sciences 746:22-31.

Dallman, M. F. & Yates, F. E. Annals of the New York Academy of Sciences 156, 696-721, (1969).

de Kloet E R, Joels M, Holsboer F (2005) Stress and the brain: from adaptation to disease. Nature reviews Neuroscience 6:463-475.

Dirks A, Groenink L, Bouwknecht J A, Hijzen T H, Van Der Gugten J, Ronken E, Verbeek J S, Veening J G, Dederen P J, Korosi A, Schoolderman L F, Roubos E W, Olivier B (2002) Overexpression of corticotropin-releasing hormone in transgenic mice and chronic stress-like autonomic and physiological alterations. Eur J Neurosci, 16, 1751-1760.

Engeszer R E, Patterson L B, Rao A A, Parichy D M (2007) Zebrafish in the wild: a review of natural history and new notes from the field. Zebrafish 4:21-40.

Groenink L, Dirks A, Verdouw P M, Schipholt M, Veening J G, van der Gugten J, Olivier B (2002) HPA axis dysregulation in mice overexpressing corticotropin releasing hormone. Biol Psychiatry, 51, 875-881.

Holsboer F, Von Bardeleben U, Gerken A, Stalla G K, Muller O A (1984) Blunted corticotropin and normal cortisol response to human corticotropin-releasing factor in depression. N Engl J Med, 311, 1127.

Holsboer and Barden, 1996 Antidepressants and hypothalamic-pituitary-adrenocortical regulation Endocr. Rev., 17 (1996), pp. 187-205

Holsboer F., The rationale for corticotropin-releasing hormone receptor (CRH-R) antagonists to treat depression and anxiety J. Psychiatr. Res., 33 (1999), pp. 181-214

Holsboer F, Ising M (2010) Stress hormone regulation: biological role and translation into therapy. Annu Rev Psychol, 61, 81-109, C101-111.

Iseki M, Matsunaga S, Murakami A, Ohno K, Shiga K, Yoshida K, Sugai M, Takahashi T, Hori T, Watanabe M (2002) A blue-light-activated adenylyl cyclase mediates photoavoidance in Euglena gracilis. Nature 415:1047-1051.

Johnson E O, Kamilaris T C, Chrousos G P, Gold P W (1992) Mechanisms of stress: a dynamic overview of hormonal and behavioral homeostasis. Neurosci Biobehav Rev 16:115-130.

Kawakami, Transgenesis and gene trap methods in zebrafish by using the Tol2 transposable element. Methods Cell Biol. 2004;77:201-22.

Kawakami K.; Tol2: a versatile gene transfer vector in vertebrates. Genome Biol. 2007; 8 Suppl 1:S7.

Kimmel C B, Ballard W W, Kimmel S R, Ullmann B, Schilling T F (1995) Stages of embryonic development of the zebrafish. Developmental dynamics: an official publication of the American Association of Anatomists 203: 253-310.

Liu N A, Huang H, Yang Z, Herzog W, Hammerschmidt M, Lin S, Melmed S (2003) Pituitary corticotroph ontogeny and regulation in transgenic zebrafish. Mol Endocrinol 17:959-966

Liu, N. A. et al. Proc Natl Acad Sci USA 108, 8414-8419, (2011).

Lowry, C. A. & Moore, F. L. General and comparative endocrinology 146, 19-27, (2006).

Lu A, Steiner M, Whittle N, Vogl A, Walser S, Ableitner M, Refojo D, Ekker M, Rubenstein J, Stella G, Singewald N, Holsboer F, Wotjak C, Wurst W, J M D (2008) Conditional mouse mutants highlight mechanisms of corticotropin-releasing hormone effects on stress-coping behavior Molecular Psychiatry, 13, 1028-1042

MacPhail R C, Brooks J, Hunter D L, Padnos B, Irons T D, Padilla S (2009) Locomotion in larval zebrafish: Influence of time of day, lighting and ethanol. Neurotoxicology 30:52-58

McEwen, B. S. & Sapolsky, R. M. Current opinion in neurobiology 5, 205-216, (1995).

Moore, F. L. & Orchinik, M. Hormones and behavior 28, 512-519, (1994).

Muller M B, Holsboer F (2006) Mice with mutations in the HPA-system as models for symptoms of depression. Biol Psychiatry, 59, 1104-1115.

Muller M B, Zimmermann S, Sillaber I, Hagemeyer T P, Deussing J M, Timpl P, Kormann M S, Droste S K, Kuhn R, Reul J M, Holsboer F, Wurst W (2003) Limbic corticotropin-releasing hormone receptor 1 mediates anxiety-related behavior and hormonal adaptation to stress. Nat Neurosci, 6, 1100-1107.

Munck A, Guyre P M, Holbrook N J (1984) Physiological functions of glucocorticoids in stress and their relation to pharmacological actions. Endocr Rev 5:25-44.

Nagel G, Ollig D, Fuhrmann M, Kateriya S, Musti A M, Bamberg E, Hegemann P. Channelrhodopsin-1: a light-gated proton channel in green algae. Science. 2002 Jun. 28; 296(5577):2395-8.

Pfaff, D., Ribeiro, A., Matthews, J. & Kow, L. M. Annals of the New York Academy of Sciences 1129, 11-25, (2008).

Prober D A, Zimmerman S, Myers B R, McDermott B M, Jr., Kim S H, Caron S, Rihel J, Solnica-Krezel L, Julius D, Hudspeth A J, Schier A F (2008) Zebrafish TRPA1 channels are required for chemosensation but not for thermosensation or mechanosensory hair cell function. The Journal of neuroscience: the official journal of the Society for Neuroscience 28:10102-10110

Prut L., Belzung C. The open field as a paradigm to measure the effects of drugs on anxiety-like behaviors: a review Eur J Pharmacol, 463 (2003), pp. 3-33;

Raber J (1998) Detrimental effects of chronic hypothalamic-pituitary-adrenal axis activation. From obesity to memory deficits. Mol Neurobiol 18:1-22.

Raadsheer F C, Hoogendijk W J G, Stam F C, Tilders F J H, Swaab D F 1994 Increased numbers of corticotropin-releasing hormone expressing neurons in the hypothalamic paraventricular nucleus of depressed patients. Neuroendocrinology 60:436-444

Refojo D, Schweizer M, Kuehne C, Ehrenberg S, Thoeringer C, Vogl A M, Dedic N, Schumacher M, von Wolff G, Avrabos C, Touma C, Engblom D, Schutz G, Nave K A, Eder M, Wotjak C T, Sillaber I, Holsboer F, Wurst W, Deussing J M (2011) Glutamatergic and dopaminergic neurons mediate anxiogenic and anxiolytic effects of CRHR1. Science, 333, 1903-1907.

Ryu M H, Moskvin O V, Siltberg-Liberles J, Gomelsky M (2010) Natural and engineered photoactivated nucleotidyl cyclases for optogenetic applications. The Journal of biological chemistry 285:41501-41508

Sandi, C. & Pinelo-Nava, M. T. Neural plasticity 2007, 78970, (2007).

Sandi, C., Venero, C. & Guaza, C. Eur J Neurosci 8, 794-800, (1996).

Sapolsky R M, Romero L M, Munck A U (2000) How do glucocorticoids influence stress responses? Integrating permissive, suppressive, stimulatory, and preparative actions. Endocr Rev 21:55-89

Schroder-Lang S, Schwarzel M, Seifert R, Strunker T, Kateriya S, Looser J, Watanabe M, Kaupp U B, Hegemann P, Nagel G (2007) Fast manipulation of cellular cAMP level by light in vivo. Nature methods 4:39-42.

Smith G W, Aubry J M, Dellu F, Contarino A, Bilezikjian L M, Gold L H, Chen R, Marchuk Y, Hauser C, Bentley C A, Sawchenko P E, Koob G F, Vale W, Lee K F (1998) Corticotropin releasing factor receptor 1-deficient mice display decreased anxiety, impaired stress response, and aberrant neuroendocrine development. Neuron, 20, 1093-1102.

Stierl M, Stumpf P, Udwari D, Gueta R, Hagedorn R, Losi A, Gartner W, Petereit L, Efetova M, Schwarzel M, Oertner T G, Nagel G, Hegemann P (2011) Light modulation of cellular cAMP by a small bacterial photoactivated adenylyl cyclase, bPAC, of the soil bacterium Beggiatoa. The Journal of biological chemistry 286:1181-1188

Swanson L W, Sawchenko P E, Rivier J, Vale W W (1983) Organization of ovine corticotropin-releasing factor immunoreactive cells and fibers in the rat brain: an immunohistochemical study. Neuroendocrinology 36:165-186

Timpl P, Spanagel R, Sillaber I, Kresse A, Reul J M, Stalla G K, Blanquet V, Steckler T, Holsboer F, Wurst W (1998) Impaired stress response and reduced anxiety in mice lacking a functional corticotropin-releasing hormone receptor 1. Nat Genet, 19, 162-166.

To T T, Hahner S, Nica G, Rohr K B, Hammerschmidt M, Winkler C, Allolio B (2007) Pituitary-interrenal interaction in zebrafish interrenal organ development. Mol Endocrinol 21:472-485.

Tsigos C, Chrousos G P (2002) Hypothalamic-pituitary-adrenal axis, neuroendocrine factors and stress. Journal of psychosomatic research 53:865-871

Wang J, Ozden I, Diagne M, Wagner F, Borton D, Brush B, Agha N, Burwell R, Sheinberg D, Diester I, Deisseroth K, Nurmikko A. Approaches to optical neuromodulation from rodents to non-human primates by integrated optoelectronic devices. Conf Proc IEEE Eng Med Biol Soc. 2011;2011:7525-8.

Weissenberger S, Schultheis C, Liewald J F, Erbguth K, Nagel G, Gottschalk A (2011) PACα- an optogenetic tool for in vivo manipulation of cellular cAMP levels, neurotransmitter release, and behavior in *Caenorhabditis elegans*. Journal of neurochemistry 116:616-625.

Wendelaar Bonga S E (1997) The stress response in fish. Physiol Rev 77:591-625.

Weninger S C, Dunn A J, Muglia L J, Dikkes P, Miczek K A, Swiergiel A H, Berridge C W, Majzoub J A (1999) Stress-induced behaviors require the corticotropin-releasing hormone (CRH) receptor, but not CRH. Proc Natl Acad Sci USA, 96, 8283-8288.

Westerfield M (2000) The zebrafish book. A guide for the laboratory use of zebrafish (*Danio rerio*). Eugene: Univ. of Oregon Press.

Wolkowitz, O. M., Burke, H., Epel, E. S. & Reus, V. I. Annals of the New York Academy of Sciences 1179, 19-40, (2009).

Wyart C, Del Bene F, Warp E, Scott E K, Trauner D, Baier H, Isacoff E Y (2009) Optogenetic dissection of a behavioural module in the vertebrate spinal cord. Nature 461: 407-410.

The invention claimed is:

1. A method of producing an inducible animal model of stress comprising genetically modifying a larval zebrafish or a transparent medaka fish to express one or more protein(s) under control of a POMC promoter, a ACTH receptor promoter (MC2R) or a promoter of a steroidogenic protein expressed specifically in the adrenal gland, said proteins being selected from the group consisting of a microbial opsin, a light-activated channel protein and a light-activated adenyl cyclase (PAC), in (a) cell(s) of the hypothalamic-pituitary-adrenal axis, wherein the protein(s) that can be activated by light are capable of inducing the release of
 (I) corticotrophin-releasing hormone (CRH) and/or arginine-vasopressin (AVP) from neurons in the paraventricular nucleus of the rostral hypothalamus;
 (ii) adrenocorticotropic hormone (ACTH) from corticotroph cells in the anterior pituitary; and/or
 (iii) glucocorticoids from cells in the adrenal cortex.

2. The method according to claim 1, wherein the protein(s) under control of a POMC promoter, a ACTH receptor promoter (MC2R) or a promoter of a steroidogenic protein expressed specifically in the adrenal gland is/are selected from the group consisting of light-activated adenylate cyclase (PAC), channelrhodopsin 1 and channelrhodopsin 2.

3. The method of claim 1, wherein the stress is chronic stress.

4. The method of claim 1, wherein the protein(s) under control of a promoter of a steroidogenic protein expressed specifically in the adrenal gland is/are selected from the group consisting of a channelrhodpsin, a halorhodopsin, a light-gated glutamate channel (LiGluR) and a light-activated adenyl cyclase (PAC).

5. The method of claim 4, wherein the promoter of a steroidogenic protein expressed specifically in the adrenal gland is selected from the group consisting of a steroidogenic factor 1 (SF1) promoter, a cytochrome p450 side chain cleavage (P450scc) gene promoter, a steoridogenic acute regulatory protein (StAR) promoter and a 3beta-hydroxysteroid dehydrogenase (3b-HSD) promoter.

6. The method of claim 5, wherein the promoter is a POMC promoter or a StAR promoter.

7. The method of claim 5, wherein the promoter is a POMC promoter.

8. The method of claim 1, wherein the promoter of a steroidogenic protein expressed specifically in the adrenal gland is selected from the group consisting of a steroidogenic factor 1 (SF1) promoter, a cytochrome p450 side chain cleavage (P450scc) gene promoter, a steoridogenic acute regulatory protein (StAR) promoter and a 3beta-hydroxysteroid dehydrogenase (3b-HSD) promoter.

9. The method of claim 8, wherein the promoter is a POMC promoter or a StAR promoter.

10. The method of claim 8, wherein the promoter is a POMC promoter.

11. The method of claim 1, in which the transparent medaka fish is a larval medaka fish.

* * * * *